(12) United States Patent
Leaner et al.

(10) Patent No.: US 9,931,339 B2
(45) Date of Patent: Apr. 3, 2018

(54) SUBSTITUTED PYRROLO[2,3-B]QUINOXALINES FOR CANCER THERAPY

(71) Applicants: University of Cape Town, Cape Town (ZA); University of Louisville Research Foundation Inc., Louisville, KY (US)

(72) Inventors: Virna Drucille Leaner, Goodwood (ZA); Pauline Janet Van Der Watt, Observatory (ZA); John Olaf Trent, Louisville, KY (US)

(73) Assignees: University of Cape Town, Cape Town (ZA); University of Louisville Research Foundation Inc., Louisville, KY (US)

( * ) Notice: Subject to any disclaimer, the term of this patent is extended or adjusted under 35 U.S.C. 154(b) by 0 days.

(21) Appl. No.: 15/500,912

(22) PCT Filed: Aug. 7, 2015

(86) PCT No.: PCT/IB2015/056019
§ 371 (c)(1),
(2) Date: Jan. 31, 2017

(87) PCT Pub. No.: WO2016/020892
PCT Pub. Date: Feb. 11, 2016

(65) Prior Publication Data
US 2017/0216285 A1 Aug. 3, 2017

Related U.S. Application Data

(60) Provisional application No. 62/034,331, filed on Aug. 7, 2014.

(51) Int. Cl.
| | | |
|---|---|---|
| *C07D 487/04* | (2006.01) |
| *A61K 31/4985* | (2006.01) |
| *A61K 31/553* | (2006.01) |
| *A61K 31/40* | (2006.01) |
| *A61K 31/5377* | (2006.01) |

(52) U.S. Cl.
CPC .......... *A61K 31/4985* (2013.01); *A61K 31/40* (2013.01); *A61K 31/5377* (2013.01); *A61K 31/553* (2013.01)

(58) Field of Classification Search
CPC .................................................... C07D 487/04
USPC ........................................................ 544/345
See application file for complete search history.

(56) References Cited

U.S. PATENT DOCUMENTS

2009/0163545 A1  6/2009  Goldfarb
2013/0225611 A1  8/2013  Weis et al.

OTHER PUBLICATIONS

Jordan, V. C. Nature Reviews: Drug Discovery, 2, 2003, 205-213.*
Hackam, et al. JAMA, 296(14), 2006, 1731-1732.*
Kozynchenko, A.P. et al: "(HET) Arylation of substituted acetonitriles 1. Synthesis of 2-amino-3 (benzimidazol-2-yl) pyrrolo [2, 3, b]-quinoxalines", Chemistry of Heterocyclic Compounds vol. 24, No. 8, Aug. 1, 1988, pp. 923-927, XP002750800, Kluwer Academic Publishers-Plenum Publishers ISSN: 0009-3122, DOI: 10.1007/BF00479351 pp. 926-927 Translated from Khimiya Geterotsikli-cheskikh Soedinenii.
Reker, Daniel et al: "Deorphaning Pyrrolopyrazines as Potent Multi-Target Antimalarial Agents", Angewandte Chemie, International Edition, 53(27), 7079-7084 CODEN: ACIEF5; ISSN: 1433-7851 Jun. 4, 2014, XP002750801, DOI: 10.1002/ANIE.201311162 10.1002/ANIE.201311162, p. 7079.

* cited by examiner

*Primary Examiner* — Douglas M Willis
(74) *Attorney, Agent, or Firm* — Workman Nydegger

(57) ABSTRACT

Compounds, including quinoxaline derivatives of formula I, for use in the treatment of cancer are described. In general, the compounds inhibit the import of proteins and transcription factors such as Kpnα, AP-1, P65, NFAT into the nucleus of a cell by inhibiting the nuclear import protein, Kpnβ1. Cancer cells have elevated levels of Kpnβ1 and the inhibition of their nuclear import activity induces cell apoptosis. The administration of an effective amount of any one of the compounds results in cell apoptosis in cancer cells, while non-cancer cells are substantially unaffected by the inhibition of Kpnβ1's nuclear import activity.

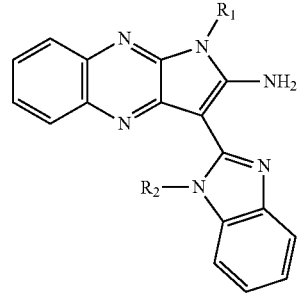

Formula I

5 Claims, 17 Drawing Sheets

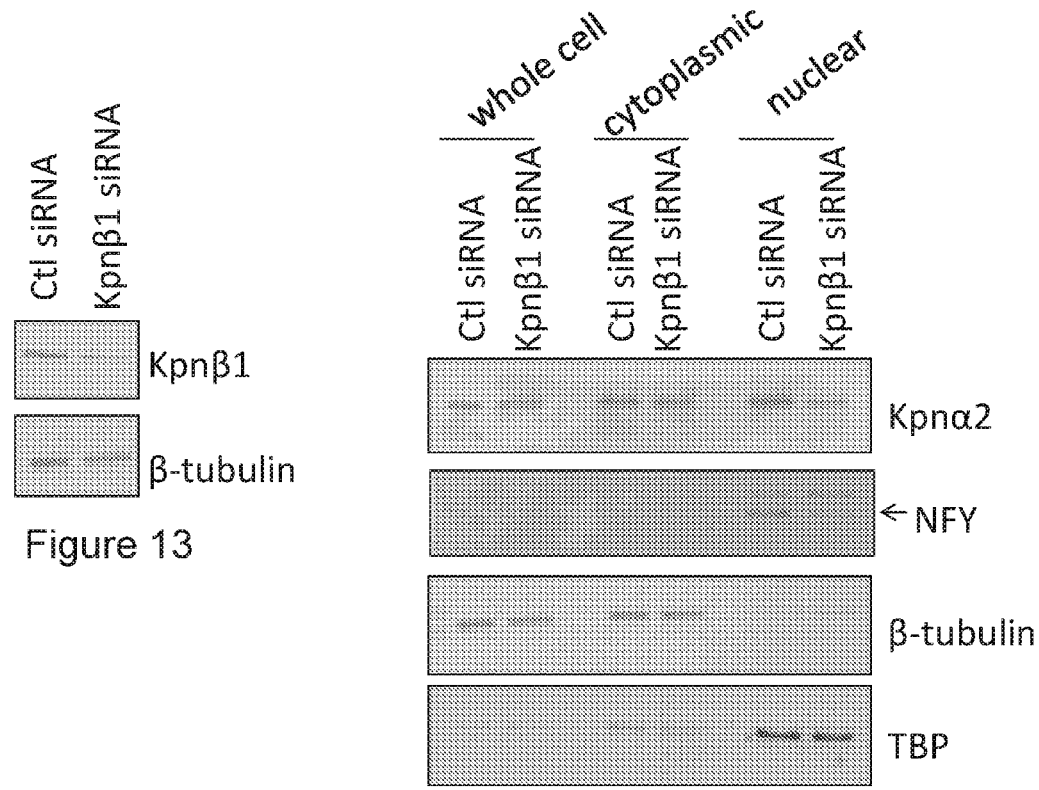
Figure 13
Figure 14
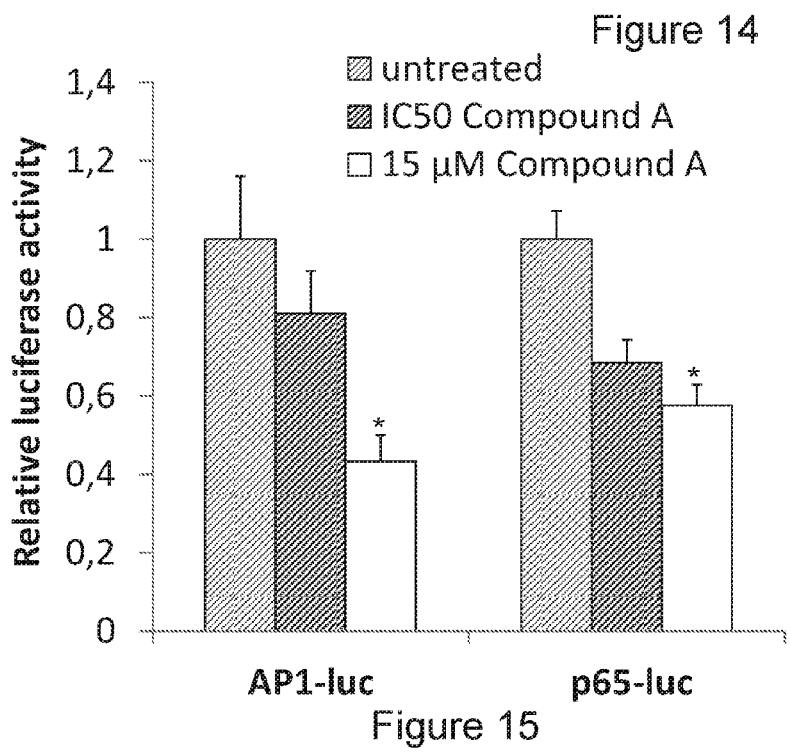
Figure 15

SUBSTITUTED PYRROLO[2,3-B]QUINOXALINES FOR CANCER THERAPY

CROSS-REFERENCE TO RELATED APPLICATIONS

The present invention is a 35 U.S.C. § 371 U.S. National Stage Application corresponding to PCT Application No. PCT/IB2015/056019, filed on Aug. 7, 2015, which claims priority to U.S. Patent Application No. 62/034,331, filed Aug. 7, 2014. The entire content of each of the aforementioned patent applications is incorporated herein by reference.

FIELD OF THE INVENTION

This invention relates to small molecule inhibitors for cancer therapy. In particular, it relates to the use of small molecules to kill cancer cells by inhibiting protein transport into the nucleus of the cells.

BACKGROUND TO THE INVENTION

Nuclear transport is the import or export of proteins across the nuclear pore complex (NPC). Nuclear transport proteins are involved in the transport process and they determine the nuclear transport capacity of a given cell. The transport capacity may have a direct impact on gene expression, signal transduction and cell growth and development.

Karyopherin beta (β) 1 (Kpnβ1) is a nuclear transport protein involved in the import of cargo proteins and RNAs across the NPC, from the cytoplasm into the nucleus. Kpnβ1 is a member of the Karyopherin β superfamily of nuclear transport proteins. There are over twenty members of the Karyopherin β protein family, which can function as either import or export receptors, mediating either the nuclear entry or exit of proteins. Kpnβ1, also known as Importin β, is a major nuclear import receptor in the cell that transports proteins containing a nuclear localisation signal (NLS) through the NPC into the nucleus. Kpnβ1-dependent nuclear import is typically characterised by the recognition of the NLS on the cargo protein by the Kpnβ1 adaptor protein, Karyopherin α (Kpnα), also known as Importin α. After cargo recognition, Kpnα binds Kpnβ1 and the trimeric complex translocates into the nucleus.

The Crm1 inhibitor Leptomycin B (LMB) is the only accepted and commercially available compound known to inhibit nuclear transport. Recently, small molecule peptidomimetic inhibitors of Kpnα/β-mediated transport were identified in an in vitro screen, however, these inhibitors have low potency and are not cell permeable, and hence no inhibition of Kpnα/β-mediated nuclear import could be observed in vivo (Ambrus G, Whitby L R, Singer E L, Trott O, Choi E, Olson A J, et al. *Small molecule peptidomimetic inhibitors of importin alpha/beta mediated nuclear transport. Bioorg Med Chem* 2010 Nov. 1; 18(21):7611-20).

Peptide inhibitors that bind Kpnα with a strong affinity have also been described, yet these do not inhibit Kpnβ1 directly (Kosugi S, Hasebe M, Entani T, Takayama S, Tomita M, Yanagawa H. *Design of peptide inhibitors for the importin alpha/beta nuclear import pathway by activity-based profiling. Chem Biol* 2008 Sep. 22; 15(9):940-9). Ivermectin is a broad-spectrum anti-parasitic that inhibits the Kpnα/β complex, but it does not appear to block import mediated by Kpnβ1 alone (Wagstaff K M, Sivakumaran H, Heaton S M, Harrich D, Jans D A. *Ivermectin is a specific inhibitor of importin alpha/beta-mediated nuclear import able to inhibit replication of HIV-1 and dengue virus. Biochem J* 2012 May 1; 443(3):851-6). Karyostatin 1A (Hintersteiner M, Ambrus G, Bednenko J, Schmied M, Knox A J, Meisner N C, et al. *Identification of a small molecule inhibitor of importin beta mediated nuclear import by confocal on-bead screening of tagged one-bead one-compound libraries. ACS Chem Biol* 2010 Oct. 15; 5(10):967-79) and Importazole (Soderholm J F, Bird S L, Kalab P, Sampathkumar Y, Hasegawa K, Uehara-Bingen M, et al. *Importazole, a small molecule inhibitor of the transport receptor importin-beta. ACS Chem Biol* 2011 Jul. 15; 6(7):700-8) are the first small molecule inhibitors of Kpnβ1 to be identified, however, their off-target effects have not yet been examined. Moreover, no inhibitor of nuclear import has as yet been tested for its anti-cancer effects. There thus remains a need for the identification of novel and effective Kpnβ1 inhibitors and for the inhibitors to be tested for their anti-cancer activities.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with a first aspect of this invention, there is provided a compound of formula I or a salt thereof for use in the treatment of cancer,

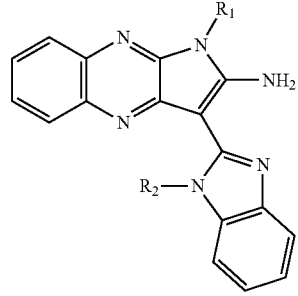

Formula I wherein $R_1$ is a C2-C5 alkyl group, branched or unbranched, optionally functionalised with a substituent selected from the group consisting of an amine, an imidazole, an alcohol or a morpholine; and wherein $R_2$ is a hydrogen or a methyl group.

Further features of this aspect of the invention provide for $R_1$ to be selected from:

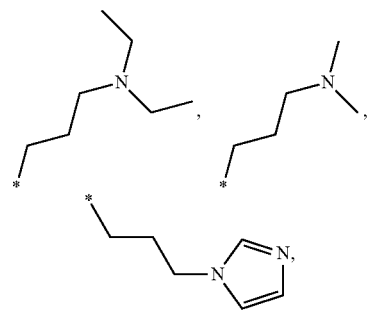

an ethyl group, a propyl group, a butyl group, an iso-butyl group, an iso-pentyl group, a propanol group and
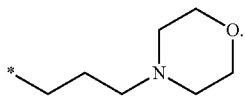
Further features of the invention provide for the compound of formula I to be selected from:
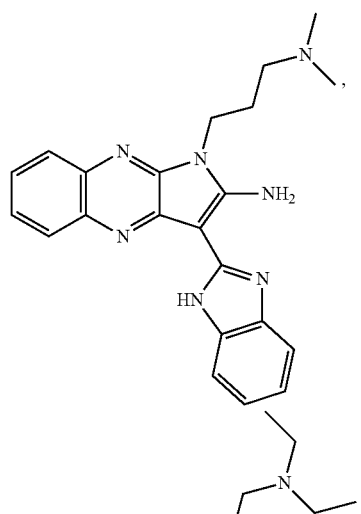
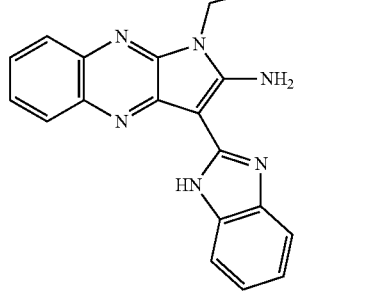
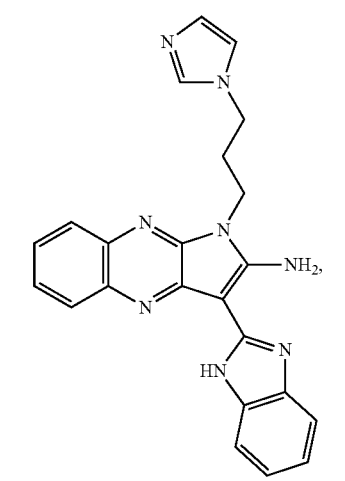
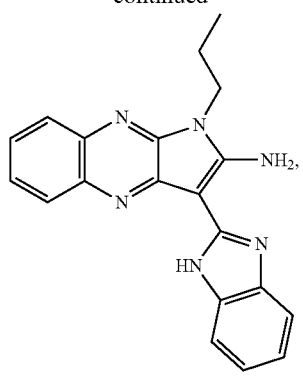
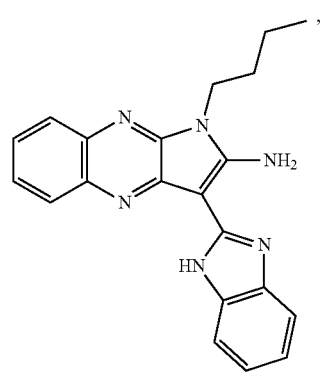
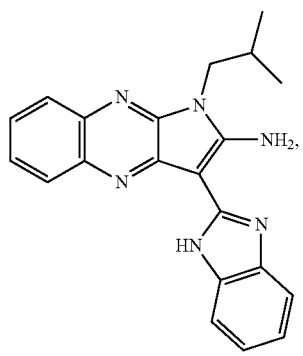
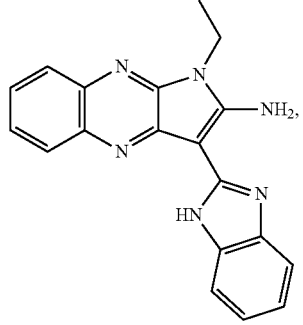

-continued

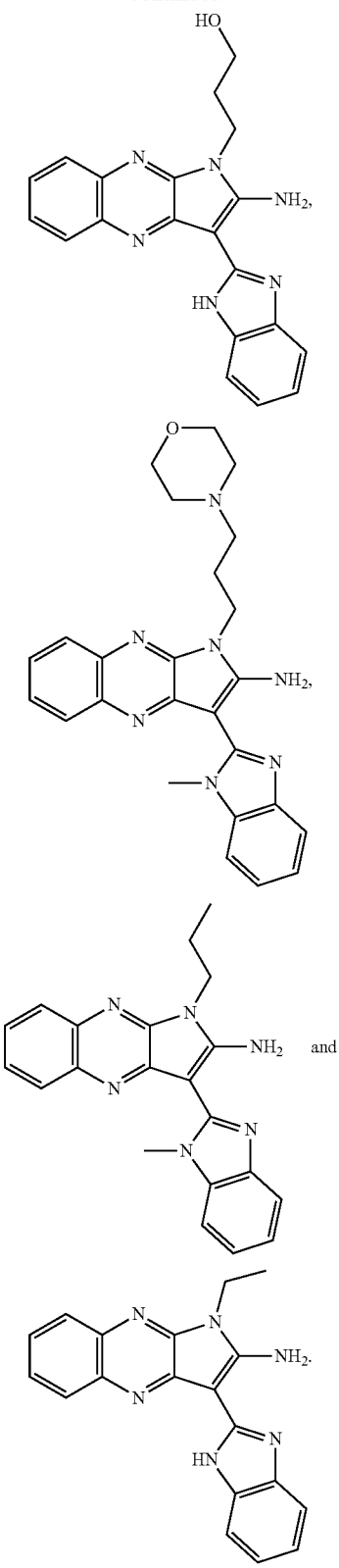

Further features of the invention provide for the compound to be used to bind to Kpnβ1 in cells and for binding to occur in a binding region of Kpnβ1 which binds karyopherin α (Kpnα) and Ran.

In accordance with a second aspect of the invention, there is provided a compound of formula II or a salt thereof for use in the treatment of cancer.

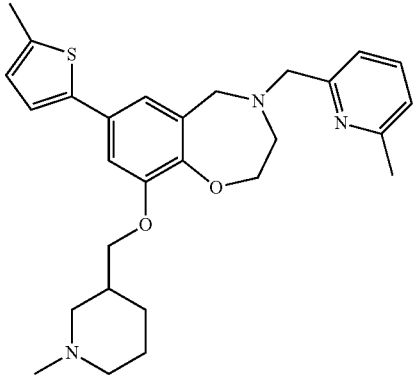

Formula II

In accordance with a third aspect of the invention, there is provided a compound of formula III, a stereoisomer or salt thereof for use in the treatment of cancer.

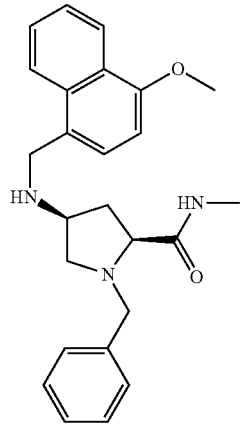

Formula III

Yet further features provide for the compounds of formula I, II, and/or III to be used to inhibit the import of proteins and transcription factors such as Kpnα, Activating Protein-1 (AP-1), NF-KappaB/P65 and Nuclear factor of activated T-cells (NFAT) into the nucleus of a cell, preferably a cancer cell.

In accordance with a fourth aspect of the invention, there is provided a compound of formula IV or a salt thereof for use in the treatment of cancer.

Formula IV

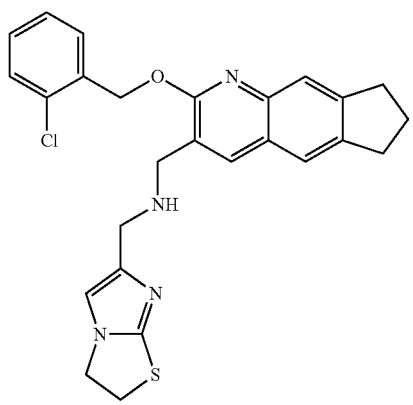

A compound of formula V or a salt thereof is provided for use in the treatment of cancer.

Formula V

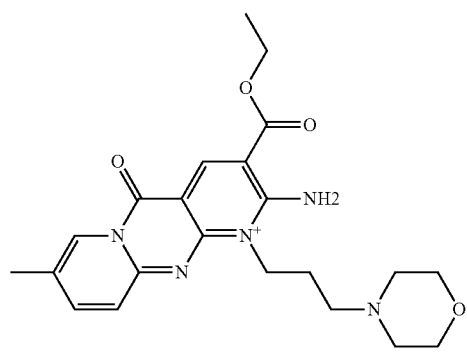

A compound of formula VI, a stereoisomer or a salt thereof is provided for use in the treatment of cancer.

Formula VI

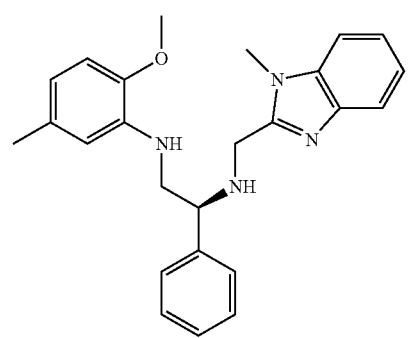

A compound of formula VII, a stereoisomer or a salt thereof is provided for use in the treatment of cancer.

Formula VII

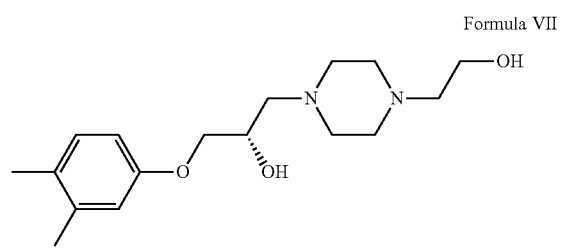 [SMILES: Cc1ccc(OC[C@@H](O)CN2CCN(CCO)CC2)cc1C]

A compound of formula VIII, a stereoisomer or a salt thereof is provided for use in the treatment of cancer.

Formula VIII

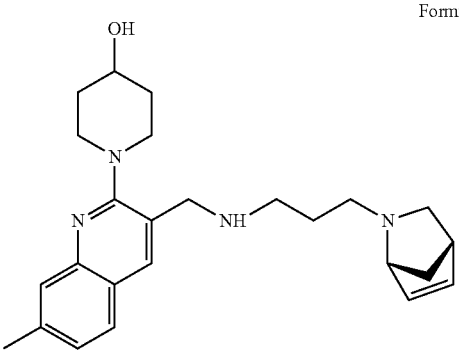

A compound of formula IX, a stereoisomer or a salt thereof is provided for use in the treatment of cancer.

Formula IX

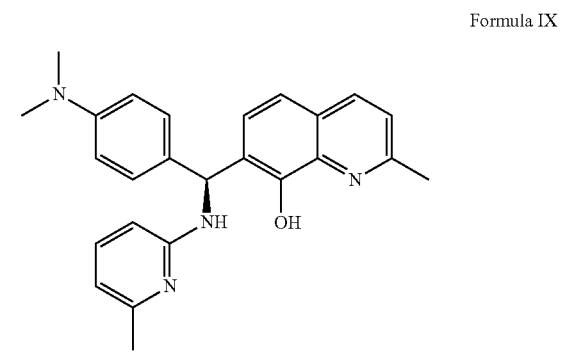

A compound of the below formula or a salt thereof is provided for use in the treatment of cancer,

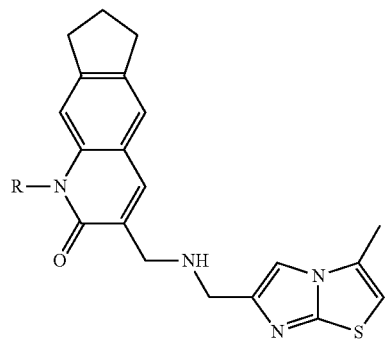

wherein R is

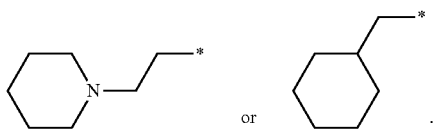 [SMILES: *CCN1CCCCC1 ; *CC1CCCCC1]

A compound of formula XII or a salt thereof is provided for use in the treatment of cancer.

Formula XII

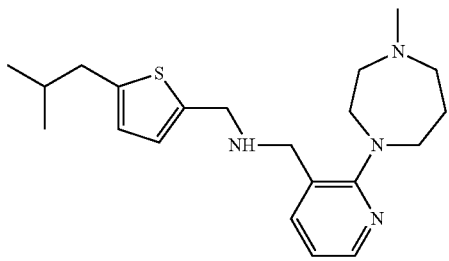

A compound of formula XIII, a stereoisomer or a salt thereof is provided for use in the treatment of cancer.

Formula XIII

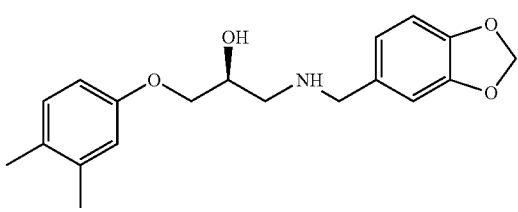

A compound of formula XIV, a stereoisomer or a salt thereof is provided for use in the treatment of cancer.

Formula XIV

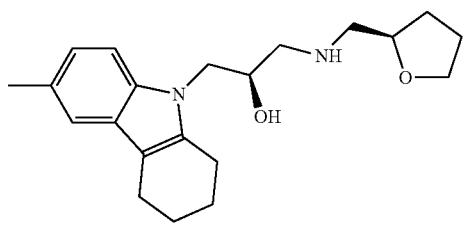

A compound of formula XV or a salt thereof is provided for use in the treatment of cancer.

Formula XV

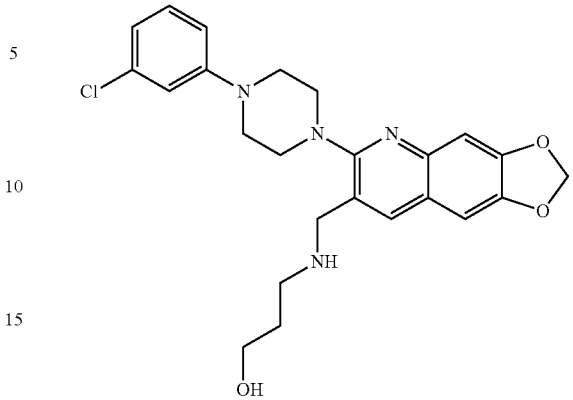

A compound of formula XVI or a salt thereof is provided for use in the treatment of cancer.

Formula XVI

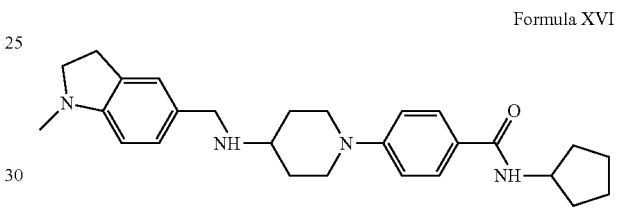

Still further features provide for the above compounds of formula I to XVI, their stereoisomers or salts to be used to induce cell apoptosis, preferably in cancer cells, after administration of an effective amount of the compound or a combination of compounds of formula I to XVI; for an effective amount to be administered at a concentration of less than 100 WI, preferably less than 50 μM.

Yet further features provide for the compounds of formula I to XVI to be used to induce cell apoptosis in cancer cells, whilst not substantially affecting non-cancer cells, by administration of an effective amount of the compound or a combination of compounds of formula I to XVI.

Still a further feature provides for the compounds of formula I to XVI as defined above to be used in treating cervical, oesophageal, ovarian, breast, and other cancers.

A further feature provides for the compounds of formula I to XVI to be used to treat a neoplasm or a cancer selected from the group consisting of gastric cancer, lung cancer, liver cancer, melanoma, Hodgkin's disease, non-Hodgkin's lymphomas, acute or chronic lymphocytic leukaemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukaemia, primary brain carcinoma, malignant melanoma, small-cell lung carcinoma, stomach carcinoma, colon carcinoma, malignant pancreatic insulinoma, malignant carcinoid carcinoma, malignant melanoma, chorio carcinoma, mycosis fungoide, head or neck carcinoma, osteogenic sarcoma, pancreatic carcinoma, acute granulocytic leukaemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, prostatic carcinoma, larynx cancer, vulvar cancer and testicular cancer.

The invention further provides a medicament characterised in that it includes as an active ingredient a compound of any of formulas I to XVI as described above, a stereoisomer or a pharmaceutically acceptable salt thereof.

The invention also provides a compound of any of formulas I to XVI, a stereoisomer or a pharmaceutically acceptable salt thereof, for use as a medicament.

The invention yet further provides for use of a compound of any of formulas I to XVI, a stereoisomer or a salt thereof in the manufacture of a medicament for use in the treatment of cancer, wherein $R_1$ is a C2-C5 alkyl group, branched or unbranched, optionally functionalised with a substituent selected from the group consisting of an amine, an imidazole, an alcohol or a morpholine; and wherein $R_2$ is a hydrogen or a methyl group.

The invention provides for a method of treating a neoplasm in a patient responsive to the inhibition of Kpnβ1 activity in the patient suffering from the neoplasm, comprising administering to the patient in need of such treatment a therapeutically effective amount of any one of or a combination of the compounds of formula I to XVI, their stereoisomers or their salts.

The invention still further provides a method of treating cancer which includes administering to a patient in need thereof a therapeutically effective amount of a compound of any one of formulas I to XVI, a stereoisomer or a pharmaceutically acceptable salt thereof, wherein $R_1$ is a C2-C5 alkyl group, branched or unbranched, optionally functionalised with a substituent selected from the group consisting of an amine, an imidazole, an alcohol or a morpholine; and wherein $R_2$ is a hydrogen or a methyl group.

BRIEF DESCRIPTION OF THE DRAWINGS

The invention will now be described, by way of example only, with reference to the accompanying representations in which:

FIG. 13 is a Western Blot showing inhibition of Kpnβ1 expression using siRNA;

FIG. 14 is a Western Blot analysis showing that siRNA knock-down of Kpnβ1 expression results in a similar decrease in Kpnα2 and NFY nuclear localisation as that observed by treatment with Compound A;

FIG. 15 is a bar graph showing a dose-dependent decrease in AP1 and p65/NFκB transcriptional activity in CaSki cells after treatment with the IC50 concentration and 15 μM of Compound A (*$p<0.05$);

DETAILED DESCRIPTION WITH REFERENCE TO THE DRAWINGS

Figure 1:
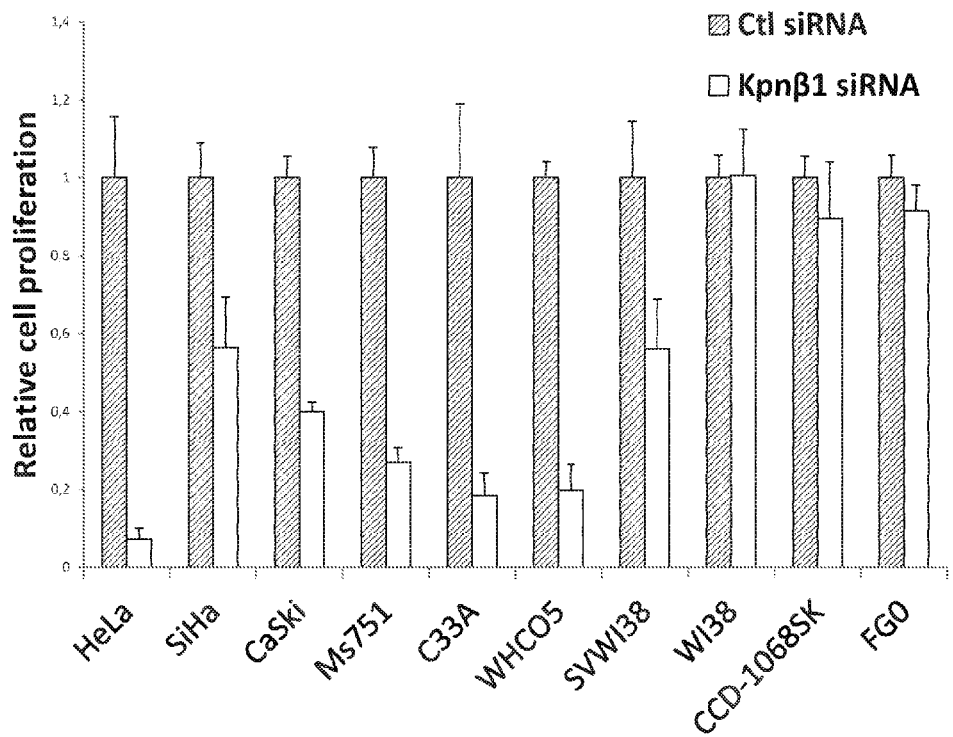
FIG. 1 is a bar graph showing the relative cell proliferation of cervical cancer (HeLa, SiHa, CaSki, Ms751, C33A), oesophageal cancer (WHCO5), transformed (SVWI38) and non-cancer (WI38, CCD-1068SK, FG0) cell lines transfected with 20 nM control siRNA (Ctl siRNA) or Kpnβ1 siRNA, wherein cell proliferation was monitored 5 days after transfection using an MTT assay (**$p<0.05$)

An in silico screening approach revealed the identity of small molecules that have the potential to bind and inhibit the Kpnβ1 transport protein. An appropriate region within the Kpnβ1 protein structure was selected as a target region. Crystal structure data of Kpnβ1 was examined and amino acid residues 331-364 of Kpnβ1 were identified as a common region required for it binding to RanGTP, SREBP-2 and Kpnα2 for the transport of classical NLS-containing cargos. A computational screen for small molecules that could bind this region of Kpnβ1 and potentially interfere with its nuclear import function was carried out. The screening was carried out using a library consisting of 14 million chemical compounds. The screened molecules were scored according to their predicted binding affinity. The molecules were scored according to their complementary shape and polarity to the above binding site and the surrounding residues. The compounds of formula I to XVI further described herein were all identified as potential inhibitors of Kpnβ1. These compounds all have at least two aromatic regions per molecule and participate in van der Waals and electrostatic interactions with complementary regions on the binding site and its surrounding residues. The compounds of formula I to XVI furthermore include hydrogen bond donors, in particular secondary and primary amine moieties, and hydrogen bond acceptors such as carbonyl or ether oxygen atoms or tertiary amines, which are suitably positioned on the respective molecules so as to participate in hydrogen bonding interactions with complementary hydrogen bond donors and acceptors that form part of the binding site and its surrounding residues on Kpnβ1. Compounds I to XVI have been shown to have anti-cancer properties so that they may be used for the treatment of cancer.

Amongst the compounds identified by the screening approach and later proven to inhibit Kpnβ1 are quinoxaline derivatives. Quinoxaline derivatives are an important class of heterocyclic compounds and the quinoxaline structure is a precursor for the assembly of a large number of derivative compounds for diverse applications. Most quinoxaline derivatives are synthetic and only a few occur naturally. Some quinoxaline derivatives are known to have biological activity and find use as antimicrobial, antiviral or antifungal agents.

Quinoxaline derivatives of general formula I or salts thereof,

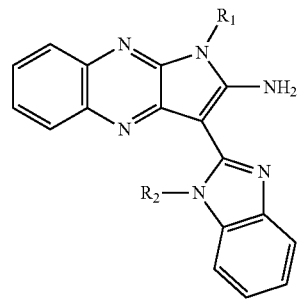

Formula I wherein $R_1$ is a C2-C5 alkyl group, branched or unbranched, optionally functionalised with a substituent selected from the group consisting of an amine, an imidazole, an alcohol or a morpholine; and wherein $R_2$ is a hydrogen or a methyl group, have now been found to have anti-cancer properties so that it may be used for cancer treatment.

The compounds of general formula I or salts thereof inhibit the import of proteins and transcription factors such as Kpnα, AP-1, P65, NFAT into the nucleus of a cell, which are known targets of the Kpnβ1 transport protein.

The compound of formula II, (2S,4S)-1-benzyl-4-{[(4-methoxynaphthalen-1-yl)methyl]amino}-N-methylpyrrolidine-2-carboxamide or one of its salts, hereinafter referred to as Compound II, and the compound of formula III, 9-[(1-methylpiperidin-3-yl)methoxy]-4-[(6-methylpyridin-2-yl) methyl]-7-(5-methylthiophen-2-yl)-3,5-dihydro-2H-1,4-benzoxazepine or one of its stereoisomer or salts, hereinafter referred to as Compound III, similarly inhibit the import of protein and transcription factors, such as NFAT and P65/NFKB into the nucleus of a cell. These compounds were also found to have anti-cancer effects so that it may be used for cancer treatment.

Formula II

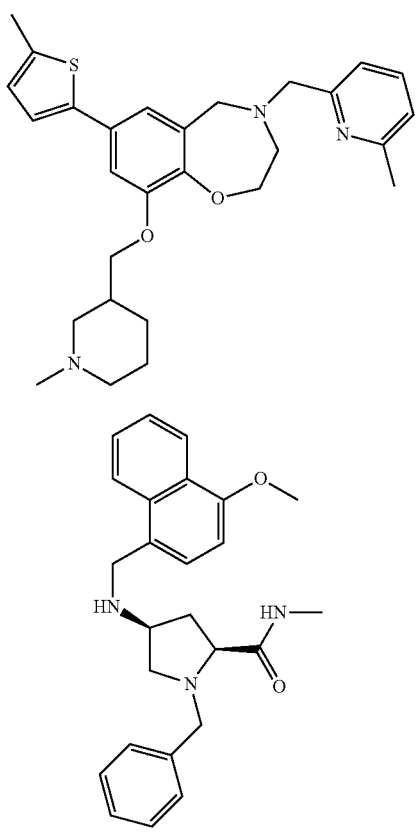

Formula III

The compound of formula IV, ({2-[(2-chlorophenyl)methoxy]-6H,7H,8H-cyclopenta[g]quinolin-3-yl}methyl)({2H,3H-imidazo[2,1-b][1,3]thiazol-6-ylmethyl})amine, or salts thereof, hereinafter referred to as Compound IV, has anti-cancer effects so that it may be used for cancer treatment.

Formula IV

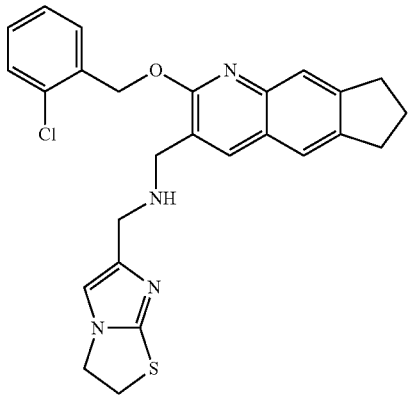

The following compounds of formula V to XVI, the stereoisomers (where applicable) or salts thereof have anti-cancer effects so that they may be used for cancer treatment:

Formula V

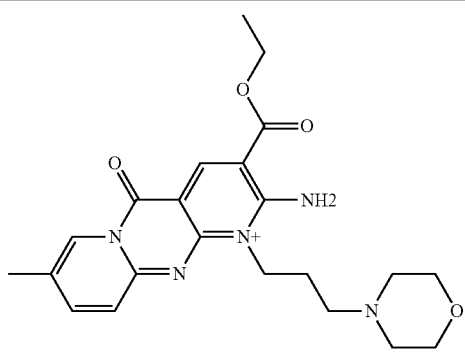 [SMILES: CCOC(=O)c1cc2c(=O)n3cc(C)ccc3nc2[n+](CCCN2CCOCC2)c1N]

ethyl 2-imino-8-methyl-1-[3-(4-morpholinyl)propyl]-5-oxo-1,5-dihydro-2H-dipyrido[1,2-a:2',3'-d]pyrimidine-3-carboxylate Formula VI

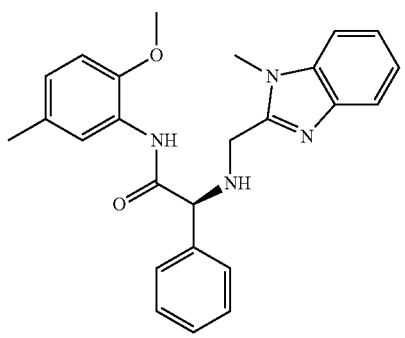 [SMILES: COc1ccc(C)cc1NC(=O)[C@@H](NCc1nc2ccccc2n1C)c1ccccc1]

(2S)-N-(2-methoxy-5-methyl-phenyl)-2-[(1-methylbenzimidazol-2-yl)methylamino]-2-phenyl-acetamide

| | | |
|---|---|---|
| Formula VII | 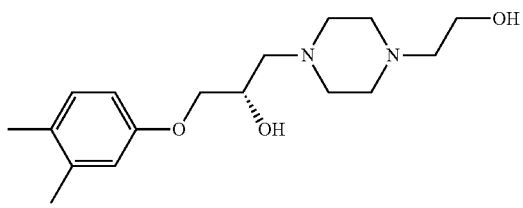 [SMILES: Cc1ccc(OC[C@@H](O)CN2CCN(CCO)CC2)cc1C] | (2S)-1-(3,4-dimethylphenoxy)-3-[4-(2-hydroxyethyl)piperazin-1-yl]propan-2-ol |
| Formula VIII | 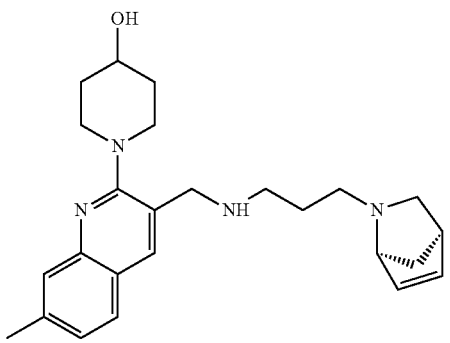 [SMILES: Cc1ccc2cc(CNCCCN3C[C@H]4C=C[C@@H]3C4)c(N3CCC(O)CC3)nc2c1] | 1-[3-[[3-[(1S,4R)-5-azabicyclo[2.2.1]hept-2-en-5-yl]propylamino]methyl]-7-methyl-2-quinolyl]piperidin4-ol |
| Formula IX | 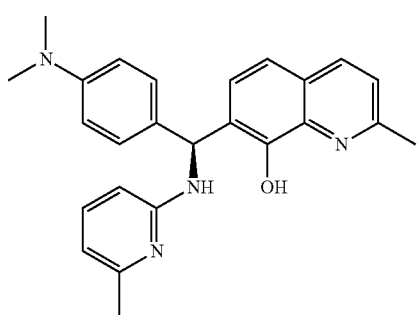 | 7-[(4-dimethylaminophenyl)-[(6-methyl-2-pyridyl)amino]methyl]-2-methyl-quinolin-8-ol |
| Formula X | 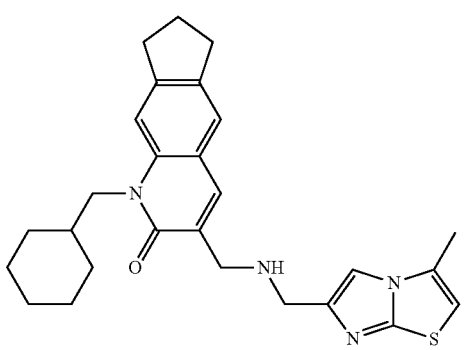 [SMILES: Cc1csc2nc(CNCc3cc4cc5c(cc4n(CC4CCCCC4)c3=O)CCC5)cn12] | 1-(cyclohexylmethyl)-3-[[(3-methylimidazo[2,1-b]thiazol-6-yl)methylamino]methyl]-7,8-dihydro-6H-cyclopenta[g]quinolin-2-one |
| Formula XI | 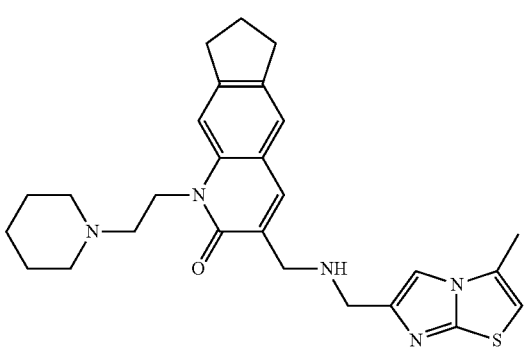 [SMILES: Cc1csc2nc(CNCc3cc4cc5c(cc4n(CCN4CCCCC4)c3=O)CCC5)cn12] | 3-[[(3-methylimidazo[2,1-b]thiazol-6-yl)methylamino]methyl]-1-[2-(1-piperidyl)ethyl]-7,8-dihydro-6H-cyclopenta[g]quinolin-2-one |

-continued

Formula XII

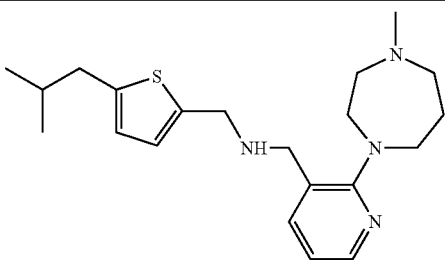

1-(5-isobutyl-2-thienyl)-N-[[2-(4-methyl-1,4-diazepan-1-yl)-3-pyridyl]methyl]methanamine Formula XIII

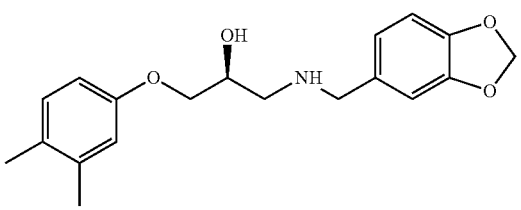 [SMILES: Cc1ccc(OC[C@@H](O)CNCc2ccc3c(c2)OCO3)cc1C]

1-(benzo[1,3]dioxol-5-methylamino)-3-(3,4-dimethylphenoxy)-propan-2-ol

Formula XIV

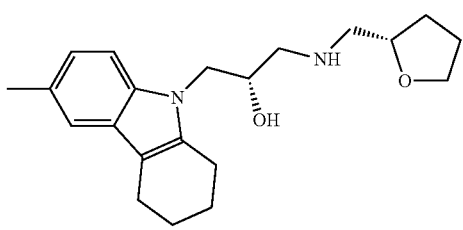 [SMILES: Cc1ccc2c(c1)c1c(n2C[C@@H](O)CNC[C@@H]2CCCO2)CCCC1]

(2S)-1-(6-methyl-1,2,3,4-tetrahydrocarbazol-9-yl)-3-[[(2S)-tetrahydrofuran-2-yl]methylamino]propan-2-ol Formula XV

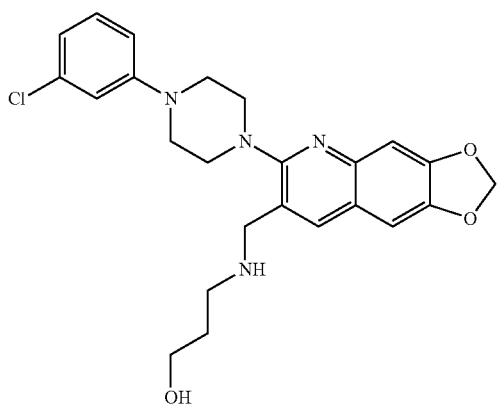 [SMILES: OCCCNCc1cc2cc3c(cc2nc1N1CCN(c2cccc(Cl)c2)CC1)OCO3]

3-[[6-[4-(3-chlorophenyl)piperazin-1-yl]-[1,3]dioxolo[4,5-g]quinolin-7-yl]methylamino]propan-1-ol Formula XVI

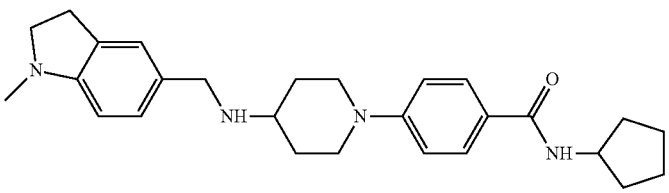 [SMILES: CN1CCc2cc(CNC3CCN(c4ccc(C(=O)NC5CCCC5)cc4)CC3)ccc21]

N-cyclopentyl-4-[4-[(1-methylindolin-5-yl)methylamino]-1-piperidyl]benzamide

The anti-cancer properties of the compounds of formula I to XVI and their mode of action will now be described further. As mentioned above all of the compounds were identified from an in silico screening for binding affinity to Kpnβ1, a nuclear transport protein.

Kpnβ1-dependent nuclear import is characterised by the recognition of the NLS on the cargo protein by the Kpnβ1 adaptor protein, Karyopherin α (Kpnα), also known as Importin α. After cargo recognition, Kpnα binds Kpnβ1 and the trimeric complex translocates into the nucleus, via Kpnβ1-interactions with the nucleoporins (Nups) that comprise the NPC. Once on the nucleoplasmic side of the NPC, the complex is dissociated by the binding of RanGTP to Kpnβ1. RanGTP and Kpnα share an overlapping binding site on the Kpnβ1 protein, yet RanGTP has a higher affinity to the site and thus displaces Kpnα, causing the cargo protein to be released (Moroianu J, Blobel G, Radu A. *Nuclear protein import: Ran-GTP dissociates the karyopherin alphabeta heterodimer by displacing alpha from an overlapping binding site on beta. Proc Natl Acad Sci USA* 1996 Jul. 9; 93(14):7059-62). Upon cargo release, RanGTP-Kpnβ1 translocates back into the cytoplasm where RanGTP is hydrolysed to RanGDP and Kpnβ1 is released for another round of nuclear transport. While Kpnβ1 transports its cargo proteins in concert with an adaptor, it can function on its own, for example in the transport of the sterol regulatory element binding protein 2 (SREBP-2) (Nagoshi E, Imamoto N, Sato R, Yoneda Y. *Nuclear import of sterol regulatory element-binding protein-2, a basic helix-loop-helix-leucine zipper (bHLH-Zip)-containing transcription factor, occurs through the direct interaction of importin beta with HLH-Zip*. Mol Biol Cell 1999 July; 10(7):2221-33).

It is known that Kpnβ1 mRNA and protein is expressed at elevated levels in cervical tumours and cell lines (Van der Watt P J, Maske C P, Hendricks D T, Parker M I, Denny L, Govender D, et al. *The Karyopherin proteins, Crm1 and Karyopherin beta1, are overexpressed in cervical cancer and are critical for cancer cell survival and proliferation*. Int J Cancer 2009 Apr. 15; 124(8):1829-4). The promoter is more active in cervical cancer cells due to its activation by the cell cycle regulator, E2F (Van der Watt P J, Ngarande E, Leaner V D. *Overexpression of Kpnbeta1 and Kpnalpha2 Importin Proteins in Cancer Derives from Deregulated E2F Activity*. PLoS One 2011; 6(11):e27723). Smith et al., (2010), found that Kpnβ1 mRNA was elevated in ovarian cancer cell lines and transformed ovarian cells and Kuusisto et al., (2012), also described elevated levels of Kpnβ1 in several transformed cell lines (Smith E R, Cai K Q, Smedberg J L, Ribeiro M M, Rula M E, Slater C, et al. *Nuclear entry of activated MAPK is restricted in primary ovarian and mammary epithelial cells*. PLoS One 2010; 5(2):e9295; Kuusisto H V, Wagstaff K M, Alvisi G, Roth D M, Jans D A. *Global enhancement of nuclear localization-dependent nuclear transport in transformed cells*. FASEB J 2012 March; 26(3):1181-93).

The elevated levels of Kpnβ1 may suggest that the Kpnβ1 protein is associated with cellular transformation and cancer. Indeed, inhibition of Kpnβ1 protein expression in cancer cells leads to apoptosis (Van der Watt et al, 2009; Angus et al., 2014), emphasizing the role of this protein in cancer development. Inhibition of Kpnβ1 protein expression in non-cancer cells, however, has only a minor effect on cell viability (Van der Watt et al, 2009; Angus L, van der Watt P J, Leaner V D. *Inhibition of the nuclear transporter, Kpnbeta1, results in prolonged mitotic arrest and activation of the intrinsic apoptotic pathway in cervical cancer cells*. Carcinogenesis 2014 Jan. 7), pointing to a potential use for Kpnβ1 as an anti-cancer therapeutic target (Van der Watt P J, Stowell C L, Leaner V D. *The nuclear import receptor Kpnbeta1 and its potential as an anti-cancer therapeutic target*. Crit Rev Eukaryot Gene Expr 2013; 23(1):1-10).

Compounds of general formula I, Compound II and Compound III inhibit nuclear import of Kpnβ1 cargo proteins such as p65/NFBK, induces cell death in cancer cells via apoptosis and inhibit cancer cell proliferation.

During the anti-cancer studies of compounds of formula I to XVI cell lines and tissue cultures were used:

Cell Lines and Tissue Culture

A GFP-Kpnα2 expression plasmid (pEGFP-C1-Kpnα2) was generated by inserting a XhoI/BamHI-cleaved human Kpnα2 cDNA fragment into pEGFP-C1 (Clontech, Mountain View, Calif., USA). The construct was stably transfected into CaSki cervical cancer cells (American Type Culture Collection, ATCC, Rockville, Md., USA) and a pool of cells expressing moderate levels of GFP-Kpnα2 was selected by FACS analysis and maintained in Dulbecco's Modified Eagle's Medium (DMEM), containing 10% Fetal Bovine Serum (FBS) (Gibco, Paisley, Scotland), 100 U/ml pencillin, 100 µg/ml streptomycin, and 200 µg/ml G418 (Sigma, St Louis, Mo., USA). All other cell lines were maintained in DMEM containing 10% FBS, 100 U/ml penicillin and 100 µg/ml streptomycin, except for normal hTERT-immortalised human oesophageal epithelial cells, EPC2-hTERT, (obtained from Prof. A. K. Rustgi (University of Pennysylvania, Philadelphia, USA)), which were cultured in keratinocyte serum-free media (KSFM), supplemented with 50 µg/ml bovine pituitary extract (BPE), 1 ng/ml Epithelial Growth Factor (EGF), and 100 U/ml pencillin and 100 µg/ml streptomycin, and MCF12A benign breast cancer cells (obtained from the ATCC), which were maintained in 50% HAMS F12 and 50% DMEM, supplemented with 5% FBS, 100 U/ml pencillin, 100 µg/ml streptomycin 20 ng/ml EGF (Gibco), 100 ng/ml Cholera Toxin (Sigma), 10 µg/ml insulin (Gibco) and 500 ng/ml hydrocortisone (Sigma). KYSE30 and KYSE150 cells were obtained from DSMZ (Berlin, Germany) and WHCO1, WHCO5 and WHCO6 oesophageal carcinoma cell lines were acquired from Dr R. Veale (Jones G J, Heiss N S, Veale R B, Thornley AL. Amplification and expression of the TGF-alpha, EGF receptor and c-myc genes in four human oesophageal squamous cell carcinoma lines. Biosci Rep 1993 October; 13(5):303-12). FG0 and DMB normal skin fibroblasts were obtained from the Department of Medicine, UCT. Unless specified above, all other cell lines were obtained from the ATCC.

IC50 Determinations were Carried Out as Follows:

Cells were plated in 96-well plates and treated with varying concentrations of a test compound for 48 hours, after which MTT dye, 3-(4,5-dimethylthiazol-2-yl)-2,5-diphenyltetrazolium bromide (Sigma), was added, and crystals solubilised 4 hours later using Solubilisation Reagent (10% SLS in 0.01 M HCl). Absorbencies were measured at 595 nm the following day using a BioTek microplate spectrophotometer (Winooski, Vt., USA) and IC50 curves were generated using GraphPad Prism.

Figure 2:
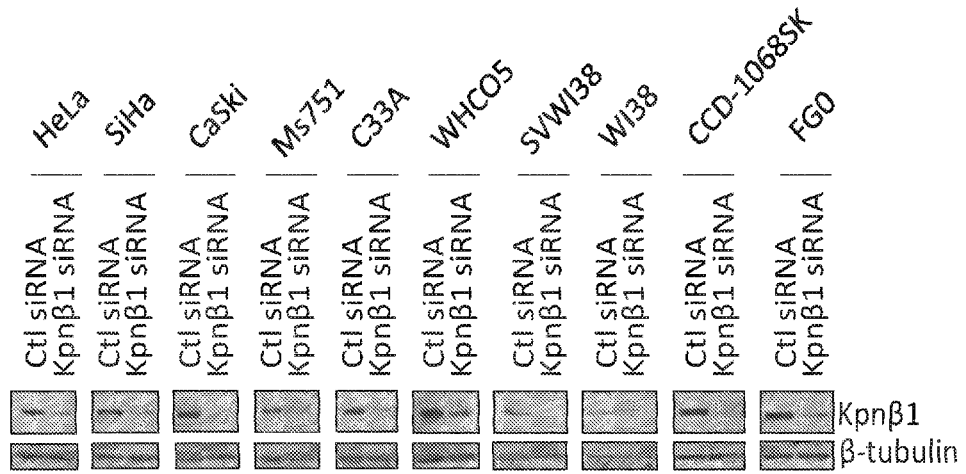
FIG. 2 is a Western Blot analysis showing effective knock-down of Kpnβ1 after Kpnβ1 siRNA transfection, wherein β-tubulin serves as a control for protein loading.

The inhibition of Kpnβ1 expression in cancer cells using siRNA results in cell death via apoptosis, while inhibition in normal cells has only a minor effect on cell biology. To verify this, a panel of cell lines were transfected with Kpnβ1 siRNA and cell viability monitored 5 days after transfection. FIG. 1 shows a significant reduction in cell number after Kpnβ1 inhibition in cervical cancer, oesophageal cancer and transformed cell lines, while non-cancer cells were relatively unaffected. Kpnβ1 knock-down in the cancer and non-cancer cells was confirmed by Western Blot analysis (FIG. 2).

The selective killing of cancer cells after Kpnβ1 inhibition with siRNA suggests that a small molecule inhibitor of Kpnβ1 may have the same effect. Especially if the inhibitor binds to the overlapping Ran- and Kpnα2-binding region of Kpnβ1 corresponding to amino acids 331-363. This region of Kpnβ1 was previously identified to be critical for its function, as its deletion resulted in an inability of Kpnβ1 to transport an NLS-HSA cargo into the nucleus (Moroianu et al., 1996).

Potential inhibitor compounds were tested for their effect on cancer cell viability, using oesophageal cancer cell lines (WHCO5 and KYSE180) and cervical cancer cell lines (HeLa and CaSki). An MTT assay for cell viability revealed that Compounds A to K displayed IC50 values of less than 50 µM (Table 1).

TABLE 1

IC50 values for quinoxaline derivatives in oesophageal cancer cell lines (WHCO5 and KYSE180) and cervical cancer cell lines (HeLa and CaSki).

| | WHCO5 | KYSE180 | HeLa | CaSki |
|---|---|---|---|---|
| Compound A | IC50 9.087 μM 95% Cl 5.113 to 16.15 μM | IC50 15.80 μM 95% Cl 12.20 to 20.47 μM | IC50 10.17 μM 95% Cl 3.980 to 26.01 μM | IC50 9.334 μM 95% Cl 6.513 to 13.38 μM |
| Compound B | IC50 5.697 μM 95% Cl 0.4393 to 73.89 μM | IC50 6.029 μM 95% Cl 0.01122 to 3240 μM | IC50 6.355 μM 95% Cl 5.680 to 7.112 μM | IC50 5.586 μM 95% Cl 0.06405 to 487.1 μM |
| Compound C | IC50 8.324 μM 95% Cl 7.672 to 9.033 | IC50 8.464 μM | IC50 7.191 μM 95% Cl 6.759 to 7.650 | IC50 9.492 μM 95% Cl 5.4416e−0.25 to 1.6558e+026 |

TABLE 1-continued

IC50 values for quinoxaline derivatives in oesophageal cancer cell lines (WHCO5 and KYSE180) and cervical cancer cell lines (HeLa and CaSki).

| | WHCO5 | KYSE180 | HeLa | CaSki |
|---|---|---|---|---|
| Compound D | IC50 12.16 μM 95% Cl 7.316 to 20.22 μM | IC50 14.78 μM 95% Cl 11.96 to 18.27 μM | IC50 8.384 μM 95% Cl 11.96 to 18.27 μM | IC50 12.21 μM 95% Cl 2.8829e−018 to 5.1693e+019 μM |
| Compound E | IC50 5.938 μM 95% Cl 3.271 to 10.78 μM | IC50 8.794 μM 95% Cl 6.512 to 11.88 μM | IC50 8.294 μM 95% Cl 6.864 to 10.02 μM | IC50 14.30 μM 95% Cl 7.489 to 27.31 μM |
| Compound F | IC50 6.591 μM 95% Cl 5.604 to 7.752 μM | IC50 5.348 μM 95% Cl 3.429 to 8.341 μM | IC50 6.769 μM 95% Cl 6.031 to 7.597 μM | IC50 7.551 μM 95% Cl 6.727 to 8.475 μM |

TABLE 1-continued

IC50 values for quinoxaline derivatives in oesophageal cancer cell lines (WHCO5 and KYSE180) and cervical cancer cell lines (HeLa and CaSki).

| | WHCO5 | KYSE180 | HeLa | CaSki |
|---|---|---|---|---|
| Compound G | IC50 6.137 μM 95% Cl 5.347 to 7.043 μM | IC50 5.506 μM 95% Cl 5.139 to 5.898 μM | IC50 6.376 μM 95% Cl 5.766 to 7.051 μM | IC50 6.172 μM 95% Cl 5.742 to 6.634 μM |
| Compound H | IC50 6.299 μM 95% Cl 4.761 to 8.334 μM | IC50 1.180 μM | IC50 4.035 μM 95% Cl 3.273 to 4.975 μM | IC50 10.03 μM 95% Cl 3.358 to 29.93 μM |
| Compound I | IC50 19.62 μM 95% Cl 7.681 to 50.09 | IC50 22.01 | IC50 15.37 95% Cl 12.35 to 19.13 | Does not converge. |

TABLE 1-continued

IC50 values for quinoxaline derivatives in oesophageal cancer cell lines (WHCO5 and KYSE180) and cervical cancer cell lines (HeLa and CaSki).

| | WHCO5 | KYSE180 | HeLa | CaSki |
|---|---|---|---|---|
| Compound J | IC50 11.76<br>95% Cl<br>9.576 to<br>14.43 | IC50 33.06<br>95% Cl<br>21.30 to<br>51.32 | IC50 22.15<br>95% Cl<br>18.24 to<br>26.89 | IC50 38.41<br>95% Cl<br>2.521 to<br>585.3 |

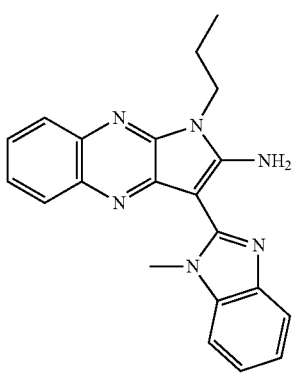

| | WHCO5 | KYSE180 | HeLa | CaSki |
|---|---|---|---|---|
| Compound K | IC50 6.789<br>95% Cl<br>2.707 to<br>17.03 | IC50 7.233<br>95% Cl<br>1.334 to<br>39.23 | IC50 4.156<br>95% Cl<br>3.048 to<br>5.667 | IC50 6.619<br>95% Cl<br>2.867 to<br>15.28 |

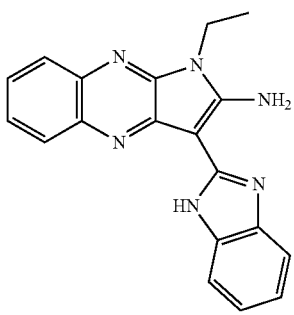

Figure 3:
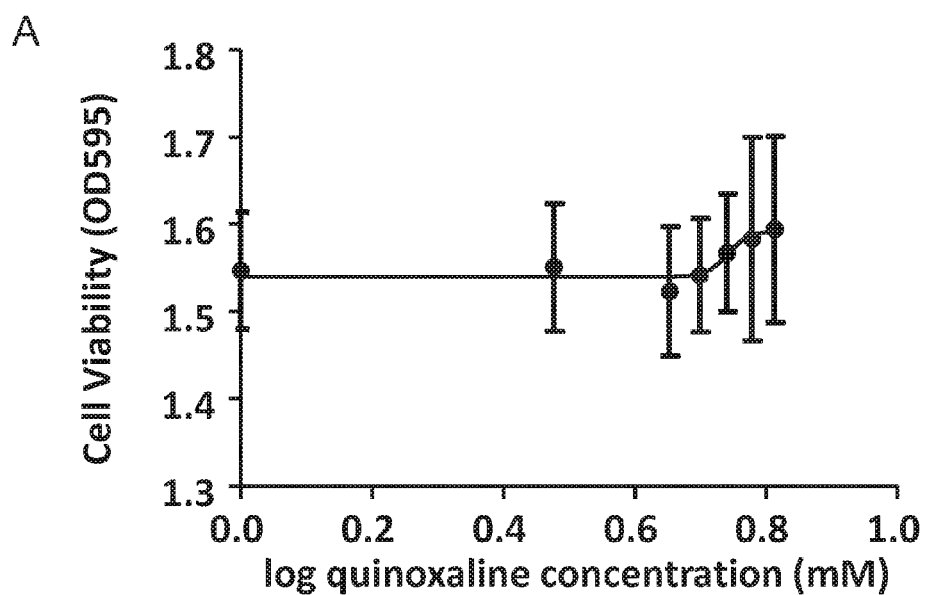
FIG. 3 is a plot of the cell viability of HeLa cancer cells treated with increasing concentrations of quinoxaline (A) and a plot of cell viability of HeLa cells treated with increasing concentrations of benzimidazole (B)
Figure 3:
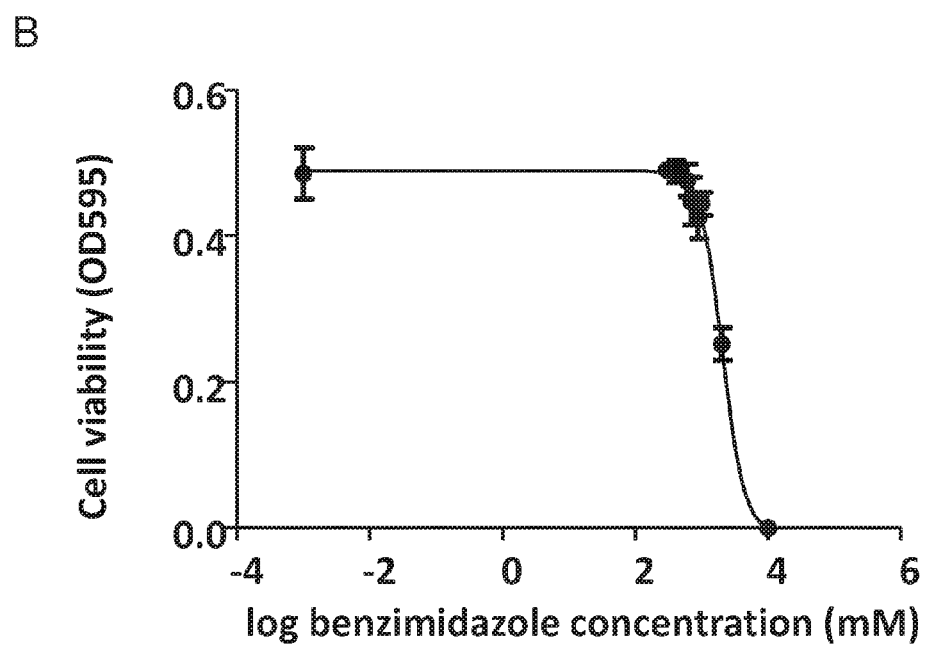

The molecular structure of Compounds A to K include a quinoxaline moiety and a benzimidazole moiety. The effect of quinoxaline and benzimidazole on the cell viability of HeLA cells were tested to determine whether the respective quinoxaline and benzimidazole molecules may have anti-cancer properties (FIG. 3). No cell-killing effect was observed in a concentration range of up to 6.5 mM quinoxaline. Benzimidazole has a cell-killing effect at a very high IC50 concentration of 2.078 mM. Benzimidazole can, however, also be considered inactive as its IC50 is well over of the range of the IC50's obtained using Compounds A to K and current chemotherapeutic drugs.

Compounds II and III were tested for their effect on cancer cell viability using the cervical cancer cell lines, CaSki and HeLa. The IC50 values on these cancerous cell lines as well as a non-cancer cell line, FG0 were determined. An MTT assay for cell viability revealed that both compounds displayed cancer cell-killing effects with IC50 values of less than 50 µM (Tables 2 and 3).

TABLE 2

IC50 values for CaSki, HeLa and FG0 cells treated with Compound II.

| Cell type | Cell line | IC50 (µM) | 95% Confidence Interval |
|---|---|---|---|
| Cancer/<br>transformed | CaSki<br>HeLa | 11.4<br>14.36 | 10.47-12.41<br>10.2-20.2 |
| Non-cancer | FG0 | 17.16 | 6.3-46.7 |

TABLE 3

IC50 values for CaSki, HeLa and FG0 cells treated with Compound III

| Cell type | Cell line | IC50 (µM) | 95% Confidence Interval |
|---|---|---|---|
| Cancer/<br>transformed | CaSki<br>HeLa | 34.1<br>19.9 | 30.97-37.56<br>16.3-24.3 |
| Non-cancer | FG0 | 44.92 | 35.4-57.1 |

Figure 4:
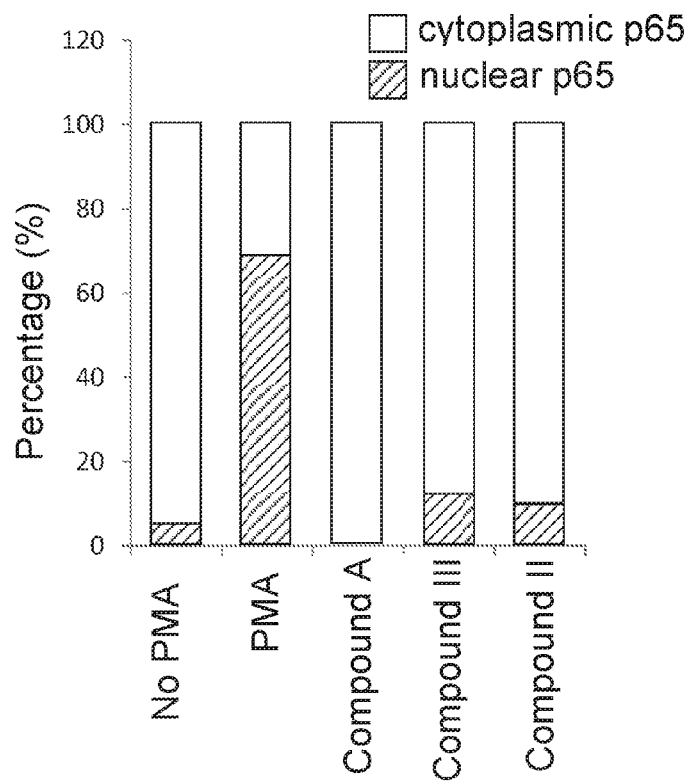
FIG. 4 is a bar graph showing the percentage of nuclear and cytoplasmic p65 in an untreated sample of cells, and samples treated with PMA, Compound A, Compound III and Compound II respectively.

Similar to Compound A, Compounds II and III inhibit the nuclear import of Kpnβ1 cargo protein as illustrated by FIG. 4 in which the percentage of nuclear p65 is shown relative to the percentage of cytoplasmic p65 when cells are left untreated, treated with PMA, Compound A, Compound III or Compound II.

Figure 5:
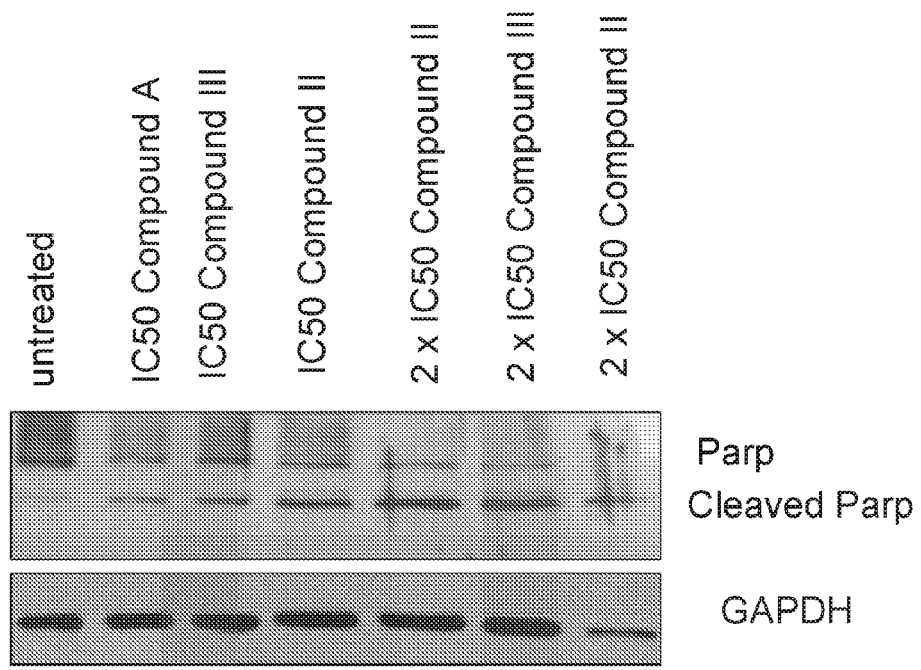
FIG. 5 is a Western Blot analysis showing that treatment with Compound A, Compound III and Compound II at IC50 and twice the IC50 concentrations results in PARP cleavage as an indicator of apoptosis.
Figure 6:
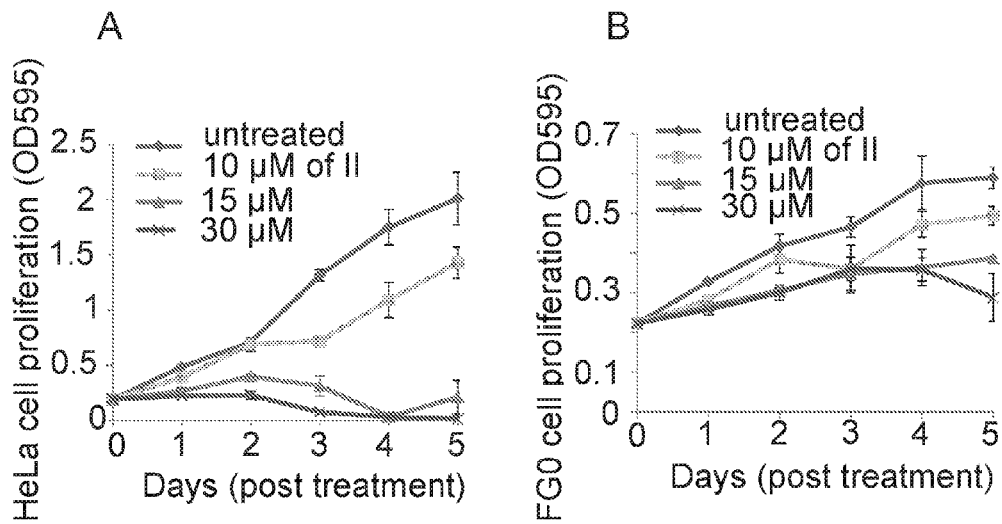
FIG. 6 is a pair of plots of cell proliferation monitored using the MTT assay of HeLa cancer cells (A) as well as FG0 non-cancer cells (B) when treated with increasing concentrations of Compound II.
Figure 7:
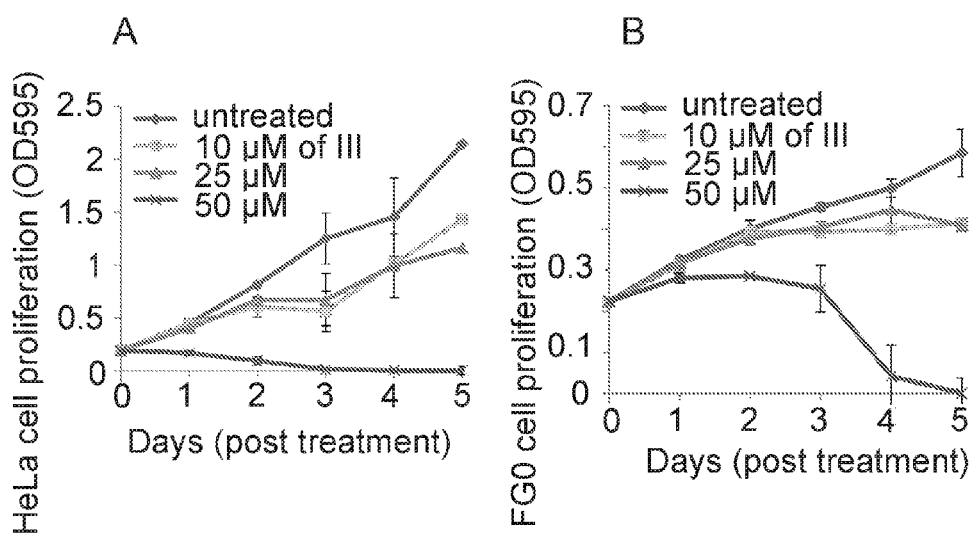
FIG. 7 is a pair of plots of cell proliferation monitored using the MTT assay of HeLa cancer cells (A) as well as non-cancer cells FG0 (B) when treated with increasing concentrations of Compound III.

Compound A and Compounds II and III induce cancer cell death via apoptosis as observed by PARP cleavage shown in FIG. 5. Compounds II and II inhibit cell proliferation as illustrated in FIGS. 6 and 7 which show cell proliferation monitored using the MTT assay of HeLa cancer cells (A) as well as FG0 non-cancer cells (B) when treated with increasing concentrations of Compound II and III.

The cell-killing effect of Compound IV was tested using a panel of cell lines of various origins. Compound IV kills cancer cell lines of cervical (CaSki, HeLa), oesophageal (WHCO5, KYSE150) and breast origin (MCF12A, MCF7, MDA-MB-231,), and a transformed cell line (SVW138) with IC50 values that range between approximately 8 and 18 µM (Table 4).

TABLE 4

IC50 values for cancer cells, transformed cells and non-cancer cells treated with Compound IV.

| Cell type | Cell line | IC50 (µM) | 95% Confidence Interval |
|---|---|---|---|
| Cancer/ transformed | CaSki | 8.69 | 8.18-9.231 |
| | HeLa | 8.621 | 7.952-9.347 |
| | KYSE150 | 11.25 | 1.628-77.68 |
| | WHCO5 | 17.95 | 17.15-18.78 |
| | MCF12A | 11.37 | 10.52-12.28 |
| | MCF7 | 13.99 | 12.09-16.18 |
| | MDA-MB-231 | 8.006 | 6.368-10.06 |
| | SVWI38 | 12.93 | 7.848-21.3 |
| Non-cancer | WI38 | 25.05 | 23.02-27.26 |
| | DMB | 8.267 | 7.848-21.3 |

Further compounds displaying cancer cell-killing effects of CasKi cervical cancer cells are listed in Table 5. The compounds listed in Table 5 have IC50 values of below 50 µM, which is within the IC50 range of Cisplatin.

TABLE 5

IC50 values for CaSki cells treated with different compounds.

| Compound number | Compound | IC50 (µM) | 95% Confidence Interval |
|---|---|---|---|
| V | ethyl 2-imino-8-methyl-1-[3-(4-morpholinyl)propyl]-5-oxo-1,5-dihydro-2H-dipyrido[1,2-a:2',3'-d]pyrimidine-3-carboxylate | 16.43 | 13.98-19.3 |
| VI | (2S)—N-(2-methoxy-5-methyl-phenyl)-2-[(1-methylbenzimidazol-2-yl)methylamino]-2-phenyl-acetamide | 19.05 | — |
| VII | (2S)-1-(3,4-dimethylphenoxy)-3-[4-(2-hydroxyethyl)piperazin-1-yl]propan-2-ol | 22.23 | 12.37-39.97 |
| VIII | 1-[3-[[3-[(1S,4R)-5-azabicyclo[2.2.1]hept-2-en-5-yl]propylamino]methyl]-7-methyl-2-quinolyl]piperidin4-ol | 24.39 | 1.59-374 |
| IX | 7-[(4-dimethylaminophenyl)-[(6-methyl-2-pyridyl)amino]methyl]-2-methyl-quinolin-8-ol | 26.64 | 24.24-29.27 |
| X | 1-(cyclohexylmethyl)-3-[[(3-methylimidazo[2,1-b]thiazol-6-yl)methylamino]methyl]-7,8-dihydro-6H-cyclopenta[g] quinolin-2-one | 26.69 | 23.76-29.97 |
| XI | 3-[[(3-methylimidazo[2,1-b]thiazol-6-yl)methylamino]methyl]-1-[2-(1-piperidyl)ethyl]-7,8-dihydro-6H-cyclopenta[g]quinolin-2-one | 26.9 | 24.46-29.58 |
| XII | 1-(5-isobutyl-2-thienyl)-N-[[2-(4-methyl-1,4-diazepan-1-yl)-3-pyridyl]methyl]methanamine | 27.38 | 26.46-28.34 |
| XIII | 1-(benzo[1,3]dioxol-5-ylmethylamino)-3-(3,4-dimethylphenoxy)-propan-2-ol | 39.52 | 35.6-43.88 |
| XIV | (2S)-1-(6-methyl-1,2,3,4-tetrahydrocarbazol-9-yl)-3-[[(2S)-tetrahydrofuran-2-yl]methylamino]propan-2-ol | 31.69 | 29.44-34.12 |
| XV | 3-[[6-[4-(3-chlorophenyl)piperazin-1-yl]-[1,3]dioxolo[4,5-g]quinolin-7-yl]methylamino]propan-1-ol | 37.74 | 33.78-42.16 |
| XVI | N-cyclopentyl-4-[4-[(1-methylindolin-5-yl)methylamino]-1-piperidyl]benzamide | 46.81 | — |

Compounds IX-XIII (in salt form) were tested on a panel of different cell lines including cancerous cell lines and normal cell lines of both epithelial and fibroblast origin. The IC50 values of the cell lines when treated with each of the respective compounds are given in Tables 6 to 10.

TABLE 6

IC50 values for cancer cells, transformed cells an non-cancer cells treated with Compound IX.

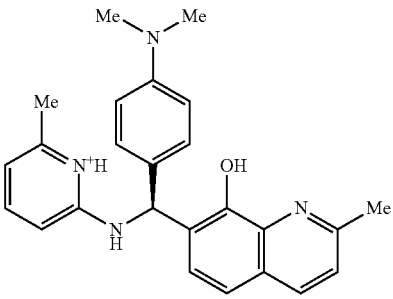

| Cell Line | IC50 (µmol/L) | 95% Confidence interval |
|---|---|---|
| CaSki | 26.64 | 24.25-29.27 |
| HeLa | 12.29 | 5.162-29.25 |
| EPC2 | 5.783 | 5.410-6.182 |
| WHCO5 | 22.38 | 17.77-28.20 |
| Kyse150 | 9.084 | 6.982-11.82 |
| MCF12A | 27.78 | 25.33-30.46 |
| MDA-MB-231 | 10.36 | 8.602-12.47 |
| MCF7 | 50.25 | 28.57-88.38 |
| DMB | 40.9 | 36.4-45.95 |
| WI38 | 20.75 | 19.28-22.39 |
| SVWI38 | 15.31 | 14.5-16.17 |

TABLE 7

IC50 values for cancer cells, transformed cells and non-cancer cells treated with Compound X.

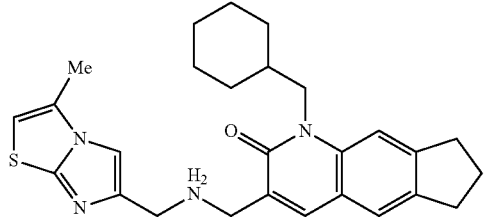

| Cell Line | IC50 (µmol/L) | 95% Confidence Interval |
|---|---|---|
| CaSki | 26.69 | 23.76-29.97 |
| HeLa | 21.47 | 17.98-25.64 |
| EPC2 | 9.371 | 6.205-14.15 |
| WHCO5 | 20.01 | 17.92-22.34 |
| Kyse150 | 32.17 | 14.39-71.89 |
| MCF12A | 11.65 | 10.07-13.47 |
| MDA-MB-231 | 22.13 | 18.6-26.32 |
| MCF7 | 23.7 | 12.94-43.41 |
| DMB | 69.27 | 44.04-108.9 |
| WI38 | 39.42 | 31.65-49.08 |
| SVWI38 | 33.49 | 30.89-36.3 |

TABLE 8

IC50 values for cancer cells, transformed cells and non-cancer cells treated with Compound XI.

| Cell Line | IC50 (μmol/L) | 95% Confidence Interval |
|---|---|---|
| CaSki | 26.9 | 24.46-29.58 |
| HeLa | 33.07 | 31.02-35.2 |
| EPC2 | not determined | |
| WHCO5 | 17.03 | 14.77-19.63 |
| Kyse150 | 40.05 | 36.16-44.36 |
| MCF12A | 61.75 | 56.47-67.52 |
| MDA-MB-231 | 32.68 | 29.86-35.76 |
| MCF7 | 95 | 73.28-123.2 |
| DMB | 31.16 | 29.46-32.97 |
| WI38 | 35.04 | 28.86-42.55 |
| SVWI38 | 41.14 | 38.38-44.10 |

TABLE 9

IC50 values for cancer cells, transformed cells and non-cancer cells treated with Compound XII.

| Cell Line | IC50 (μmol/L) | 95% Confidence Interval |
|---|---|---|
| CaSki | 27.38 | 26.46-28.34 |
| HeLa | 23.09 | 15.13-35.23 |
| EPC2 | 41.58 | 31.46-54.95 |
| WHCO5 | 20.28 | 17.66-23.28 |
| Kyse150 | 25.53 | 23.26-28.02 |
| MCF12A | 34.15 | 28.72-40.60 |
| MDA-MB-231 | 30.02 | 28.29-31.84 |
| MCF7 | 44.86 | 40.63-49.52 |
| DMB | 56.96 | 45.83-70.77 |
| WI38 | 33.75 | 25.52-44.63 |
| SVWI38 | 31.31 | 29.32-33.43 |

TABLE 10

IC50 values for cancer cells, transformed cells and non-cancer cells treated with Compound XIII.

| Cell Line | IC50 (μmol/L) | 95% Confidence Interval |
|---|---|---|
| CaSki | 39.52 | 35.6-43.88 |
| HeLa | 53.57 | 45.32-63.32 |
| EPC2 | 34.64 | 29.58-40.56 |
| WHCO5 | 40.05 | 36.56-43.87 |
| Kyse150 | 98.39 | 90.56-106.9 |
| MCF12A | 49.31 | 41.14-59.10 |
| MDA-MB-231 | 32.97 | 26.39-41.18 |
| MCF7 | 44.52 | 40.56-48.87 |
| DMB | 93 | 82.36-105 |
| WI38 | 36.23 | 32.94-39.84 |
| SVWI38 | 42.06 | 37.96-46.61 |

In order to demonstrate the anti-cancer properties of compounds of general formula I, 3-(1H-benzimidazol-2-yl)-1-(3-dimethylaminopropyl)pyrrolo[5,4-b]quinoxalin-2-amine (hereinafter referred to as "Compound A"), and its inhibitory action on import proteins will now be described in more detail.

The following methods were used to study the inhibitory action of Compound A:

Fluorescence Microscopy

CaSki cells stably expressing GFP-Kpnα2 were grown on glass coverslips and treated with either the IC50 or 20 μM of Compound A for 24 hours. For controls, equivalent volumes of DMSO were used. Cells were fixed with 4% paraformaldehyde prior to fluorescence microscopy and cell nuclei were stained with 0.5 μg/ml DAPI. Due to fluorescence emitted by Compound A in the GFP channel, the Compound A signal had to be excluded from the GFP signal by separating the emission spectra. A Zeiss LSM 510 Meta confocal microscope was used and images captured using the ZEN 2009 camera with associated AxioVision software (version 4.7). Pictures were edited using the Zeiss image browser. For quantification, 100 cells from each condition were analysed using Image J.

Nuclear and Cytoplasmic Protein Extraction

Nuclear and cytoplasmic protein fractionation was performed using the NE-PER Nuclear Protein Extraction Kit (ThermoScientific, Rockford, Ill., USA), according to the manufacturer's instructions. CaSki cells were either treated with the IC50 of Compound A for 48 hours, or transfected with 20 nM control siRNA (sc-37007, Santa Cruz Biotechnology) or Kpnβ1 siRNA (sc-35736, Santa Cruz Biotechnology) for 96 hours, prior to protein extraction. Western Blot analysis was performed using a goat anti-Karyopherin α2 (C-20) antibody (sc-6917, Santa Cruz Biotechnology), and a rabbit anti-NFYA (H-209) antibody (sc-10779, Santa Cruz Biotechnology). An anti-β-tubulin (H-235) antibody (sc-9104, Santa Cruz Biotechnology) was used to control for cytoplasmic protein loading and a rabbit anti-TATA-box binding protein (TBP) (N-12) antibody (sc-204, Santa Cruz Biotechnology) to control for nuclear protein loading. Densitometry was performed using Image J.

Luciferase Assays

To assay for AP-1 and p65 luciferase activities, 40 000 CaSki cells were plated in 24-well plates, and transfected with 50 ng of an AP1 luciferase reporter (containing four copies of the AP-1 binding site) or 50 ng of a p65 luciferase reporter (containing five copies of the p65 binding site, Clontech, Calif., USA) and 5 ng pRL-TK (encoding *Renilla* luciferase, Promega), using 0.16 µl TransFectin™ lipid reagent (Bio-Rad, Hercules, Calif., USA). The following day cells were treated with 10 or 15 µM Compound A. Luciferase activity was measured 24 hours after Compound A treatment using the Dual-Luciferase® Reporter assay system (Promega, Madison, Wis., USA), according to the manufacturers' instructions. Luciferase readings were measured using the Veritas™ microplate luminometer (Promega) and luciferase readings were normalised to *Renilla* luciferase in the same extract.

To assay for NFAT luciferase activity, 30 000 HeLa cells were plated per well in 24-well plates, and transfected with 50 ng GFP-NFAT plasmid (Addgene plasmid #24219, gift of Jerry Crabtree (Beals C R, Clipstone N A, Ho S N, Crabtree G R. Nuclear localization of NF-ATc by a calcineurin-dependent, cyclosporin-sensitive intramolecular interaction. Genes Dev 1997 Apr. 1; 11(7):824-34)), 50 ng NFAT-luciferase (Addgene plasmid #10959, gift of Toren Finkel (Ichida M, Finkel T. Ras regulates NFAT3 activity in cardiac myocytes. J Biol Chem 2001 Feb. 2; 276(5):3524-30)), and 5 ng pRL-TK, using 0.4 µl Genecellin™ Transfection Reagent (Celtic Molecular Diagnostics, South Africa). The NFAT-luciferase reporter plasmid contains three tandem repeats of a 30 bp fragment of the IL-2 promoter known to bind NFAT. The following day cells were treated with 10 or 15 µM Compound A and after an overnight incubation, stimulated with 100 nM TPA (Sigma) and 1.3 µM Ionomycin (Santa Cruz Biotechnology, Santa Cruz, Calif., USA) for 5 hours, following which luciferase activity was measured.

Cell Proliferation Assays

To assay for cell proliferation after Compound A treatment, 5000 cells/well were plated in 96-well plates and treated with 5, 10 or 15 µM Compound A, after which cell proliferation was monitored every 24 hours for four days, using MTT.

Cell Cycle Analysis

CaSki cells were plated in 60 mm dishes and treated with the appropriate concentration of Compound A. Cells were harvested 24 hours after treatment, and fixed in 100% ethanol, after which they were stained with Propidium Iodide and the cell cycle profiles analysed using a BD flow cytometer (BD Biosciences, NJ, USA). Data analysis was performed using ModFit 3.3 software.

Parp Cleavage Analysis

CaSki cells were treated with varying concentrations of Compound A for 12 hours, following which cells and cell floaters were harvested using RIPA buffer (10 mM Tris-Cl, pH 7.4, 150 mM NaCl, 1% sodium deoxycholate, 0.1% SDS, 1% Triton X-100, 1× complete protease inhibitor cocktail (Roche, Mannheim, Germany)) and Western Blot analysis performed, using a rabbit anti-Parp1/2 (H-250) antibody (sc-7150).

Mitochondrial and Cytoplasmic Protein Extractions

Cells were grown in 10 cm plates and treated with varying concentrations of Compound A for 24 hours. Cells were lysed in subcellular fractionation buffer (250 mM sucrose, 20 mM HEPES, 10 mM KCl, 1.5 mM $MgCl_2$, 1 mM EDTA, 1 mM EGTA, 1 mM DTT and 1× complete protease inhibitor cocktail (Roche)), passed through a 25G needle and incubated on ice for 20 minutes. The nuclear pellet was obtained after centrifugation at 720 g for 5 minutes. The supernatant was further centrifuged at 10,000 g and the resulting supernatant used as the cytoplasmic fraction. The pellet containing the mitochondrial fraction was washed in subcellular fractionation buffer and passed through a 25G needle. The mitochondrial fraction was pelleted at 10,000 g and resuspended in RIPA buffer. Western Blot analysis was performed using a mouse anti-Cytochrome C antibody (BD Pharmingen, San Diego, Calif.), and anti-β-tubulin (H235) (sc-9104, Santa Cruz) and anti-Pereroxiredoxin-3 (PRDX-3) (P1247, Sigma) antibodies were used as protein loading controls for cytoplasmic and mitochondrial fractions, respectively.

Xenograft Tumour Models

WHCO6 cells were harvested and resuspended in PBS. For tumour inoculation, cancer cells (5×106 per mouse) were s.c. implanted into the hind flanks of female nude mice. Once tumours had reached a palpable size, drug treatment was initiated, where tumour-bearing mice were randomized and dosed i.p. with either vehicle (DMSO) or Compound A (50 mg/kg), every 2-3 days for 3 weeks. Tumour volumes were measured twice a week, using calipers, and tumour volume estimated using the following formula: volume=(length×width×width)/2. Mice were sacrificed 3 weeks after the commencement of drug treatment.

Statistical Analysis

For all data comparisons, the Student's t test was performed using Microsoft Excel, except for the in vivo study, in which case the two-way ANOVA test was performed using GraphPad Prism 5. A p value of <0.05 was considered statistically significant.

Compound A is a quinoxaline derivative with molecular formula $C_{22}H_{23}N_7$ and a molecular weight of 385.465 g/mol. The compound is obtained in powder form and is soluble in dimethylsulfoxide (DMSO).

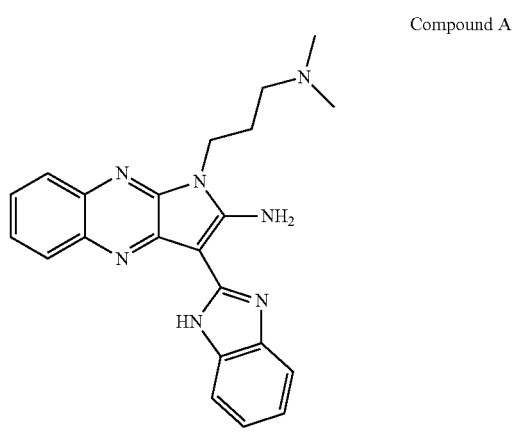 [SMILES: CN(C)CCCn1c(N)c(-c2nc3ccccc3[nH]2)c2nc3ccccc3nc21]

Compound A

It will be appreciated by someone skilled in the art that compounds of general formula I and their salts, wherein $R_1$ is a C2-C5 alkyl group, branched or unbranched, optionally functionalised with a substituent selected from the group consisting of an amine, an imidazole, an alcohol or a morpholine; and wherein $R_2$ is a hydrogen or a methyl group will have the same or a very similar mode of action and cancer cell-killing effects as that of Compound A.

The mechanism of action and cancer cell-killing effect of Compound A is described further in the below results section. It will be appreciated by someone skilled in the art that Compounds B to K, which are structurally similar to Compound A have the same or very similar inhibition activity and cancer cell-killing effects as that of Compound A. Compounds A to K have a substantially similar shape and polarity which is complementary to the binding site on Kpnβ1 and its surrounding residues. It will be appreciated by someone skilled in the art that Compounds A to K participate in substantially the same van der Waals interactions and hydrogen bonding interactions with the binding site and its surrounding residues so as to associate with or bind to it and inhibit Kpnβ1 activity, thereby inducing apoptosis in cancer cells.

Results

Figure 8:
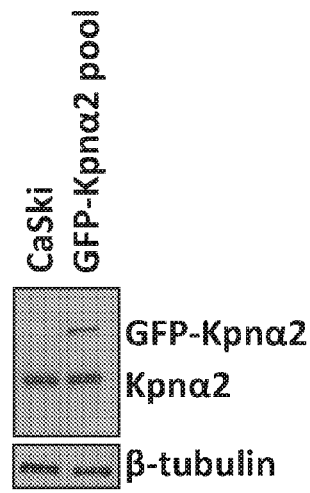
FIG. 8 is a Western Blot analysis showing GFP-Kpnα2 expression in CaSki cells stably transfected with pEGFP-Kpnα2, wherein endogenous Kpnα2 levels are indicated and β-tubulin serves as a control for protein loading.
Figure 9:
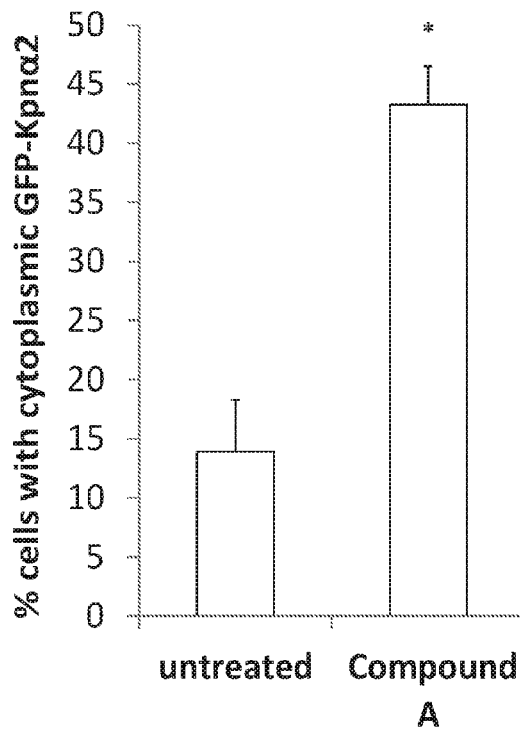
FIG. 9 is a bar graph showing the percentage of cells with cytoplasmic GFP-Kpnα2 fluorescence in an untreated sample of cells and a sample of cells treated with 10 μM Compound A (*$p<0.05$)
Figure 10:
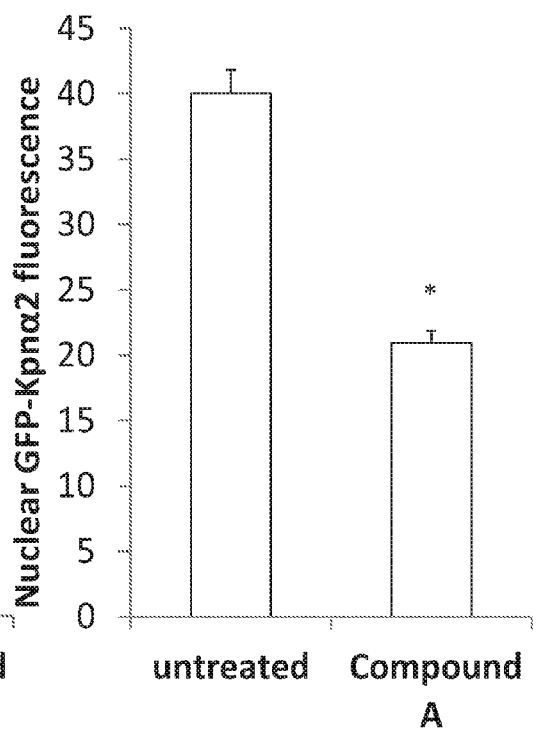
FIG. 10 is a bar graph of the nuclear GFP-Kpnα2 fluorescence in an untreated sample of cells and a sample of cells treated with 10 μM Compound A (*$p<0.05$)

GFP-Kpna2 Nuclear Translocation Prevention Compound A with cell-killing ability was tested for its ability to block nuclear import using a fluorescence-based screening assay. The assay was based on the fact that Kpnα enters the nucleus in a complex with Kpnβ1. Kpnα2 (Impα1 or Rch1) was GFP-tagged (FIG. 8) and its localisation monitored after treatment with the various compounds, via fluorescence microscopy. It was anticipated that GFP-Kpnα2 localisation would be predominantly nuclear; and that after treatment of cells with compounds that are effective at blocking Kpnβ1-mediated nuclear import, GFP-Kpnα2 would be unable to enter the nucleus and would accumulate in the cytoplasm. Treatment with this compound resulted in the mislocalisation of GFP-Kpnα2 from the nucleus to the cytoplasm. Compound A inhibits nuclear import. It was noted that Compound A fluoresced itself, and thus the compound fluorescence signal had to be excluded from the GFP-Kpnα2 signal by separating the emission spectra. The number of cells containing cytoplasmic GFP-Kpnα2 were counted (over 100 cells were counted per condition), and a significant increase observed after Compound A treatment (FIG. 9), as well as a significant decrease in the GFP-Kpnα2 nuclear fluorescence signal (FIG. 10).

Reduction of the Nuclear Import of Endogenous Kpna2 and NFY

Figure 11:
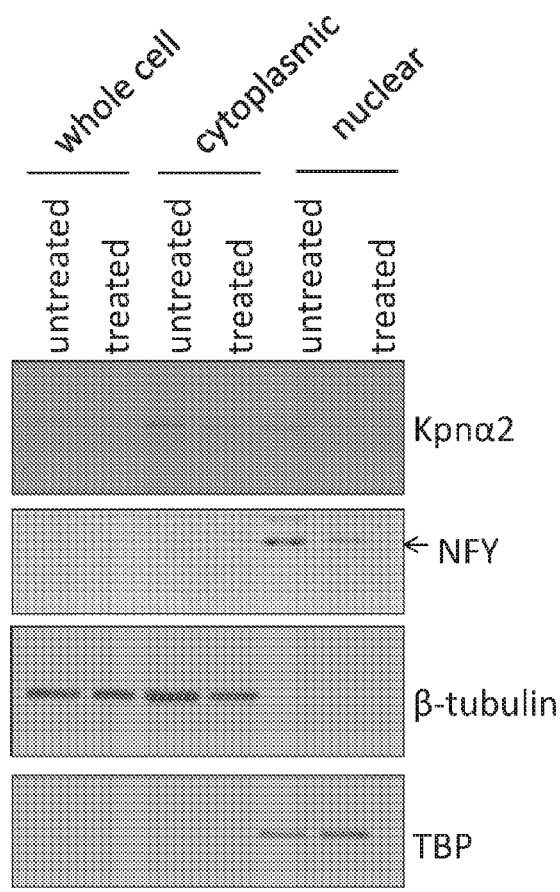
FIG. 11 is a Western Blot showing Kpnα2 and NFY cytoplasmic and nuclear localisation in protein lysates of untreated cells and cells treated with Compound A, wherein β-tubulin was used as a cytoplasmic loading control and rabbit anti-TATA-box binding protein (TBP) as a nuclear loading control.

In order to confirm that Compound A blocks nuclear import, an independent assay was performed where nuclear and cytoplasmic protein fractions were isolated after treatment of cells with Compound A. Western Blot analysis was performed to determine the localisation of endogenous Kpnα2, as it was expected that treatment with an effective inhibitor of nuclear import would prevent endogenous Kpnα2 from entering the nucleus. Compound A treatment resulted in a decrease in the amount of Kpnα2 in the nucleus (FIG. 11). However, the amount of Kpnα2 in the cytoplasm was not increased as expected, possibly due to enhanced degradation of Kpnα2 when unable to enter the nucleus, or alternatively, due to it becoming attached to the nuclear envelope and thus not being accounted for in either nuclear or cytoplasm protein fractions.

Figure 12:
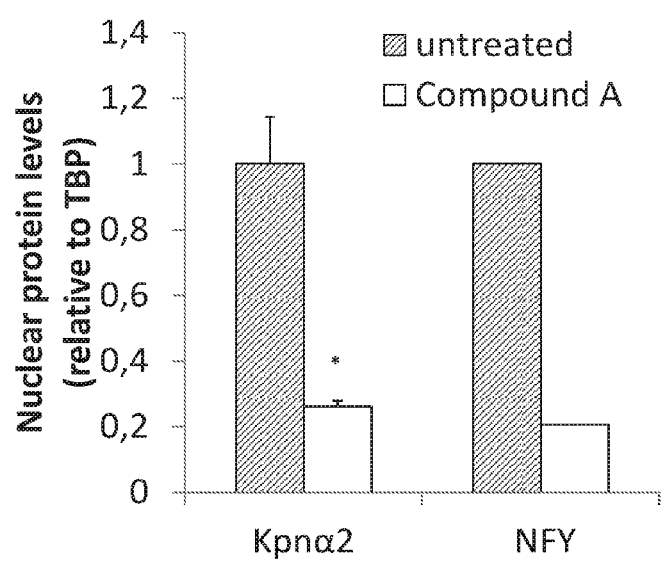
FIG. 12 is a bar graph showing the Kpnα2 and NFY nuclear protein levels in untreated cells and cells treated with Compound A relative to TBP in the same extract, wherein experiments were performed in triplicate and the mean and the standard error of the mean is shown (*$p<0.05$)

The localisation of an independent Kpnβ1 cargo, NFY-A (Kahle J, Baake M, Doenecke D, Albig W. *Subunits of the heterotrimeric transcription factor NF-Y are imported into the nucleus by distinct pathways involving importin beta and importin 13*. Mol Cell Biol 2005 July; 25(13):5339-54) was also investigated, and was similarly found to decrease in the nuclear fraction after Compound A treatment, supporting the finding that Compound A was likely blocking nuclear import (FIG. 11). Densitometric quantification of Kpnα2 and NFY levels in repeat experiments confirmed a significant reduction in nuclear protein levels after Compound A treatment (FIG. 12). To verify that the banding pattern observed after Compound A treatment was as expected after inhibition of Kpnβ1, Kpnβ1 was silenced using siRNA, and nuclear and cytoplasmic protein fractions isolated for Western Blot analysis. The amount of Kpnα2 was less in the nucleus after Kpnβ1 inhibition using siRNA supporting the results with Compound A. Similarly, the amount of NFY was less in the nuclear fraction after Kpnβ1 siRNA transfection (FIGS. 13 and 14).

Prevention of Transcription Factor Access to the Nucleus

Since an inhibitor of Kpnβ1-mediated nuclear import would likely affect the import of transcription factors into the nucleus, luciferase assays were performed to assay for AP-1 and p65 nuclear activities, after Compound A treatment, as transcription factors have been shown to rely on Kpnβ1 for nuclear import (Forwood J K, Lam M H, Jans D A. *Nuclear import of Creb and AP-1 transcription factors requires importin-beta 1 and Ran but is independent of importin-alpha*. Biochemistry 2001 May 1; 40(17):5208-17; Liang P, Zhang H, Wang G, Li S, Cong S, Luo Y, et al. *KPNB1, XPO7 and IPO8 Mediate the Translocation of NF-kappaB/p65 into the Nucleus*. Traffic 2013 November; 14(11):1132-43). AP-1 and p65-luciferase activities were measured after Compound A treatment of CaSki cells, and as anticipated, both decreased in a dose-dependent manner after treatment (FIG. 15).

The transcription factor NFAT also shuttles between the nucleus and the cytoplasm in a Kpnβ1-dependent manner (Ishiguro K, Ando T, Maeda O, Ohmiya N, Niwa Y, Goto H. *Acetate inhibits NFAT activation in T cells via importin beta 1 interference*. Eur J Immunol 2007 August; 37(8):2309-16) and Crm1-dependent manner (Kehlenbach R H, Dickmanns A, Gerace L. *Nucleocytoplasmic shuttling factors including Ran and CRM1 mediate nuclear export of NFAT In vitro*. J Cell Biol 1998 May 18; 141(4):863-74). However, its nuclear-cytoplasmic transport is unique in that it is regulated via calcium exposure (Shibasaki F, Price E R, Milan D, McKeon F. *Role of kinases and the phosphatase calcineurin in the nuclear shuttling of transcription factor NF-AT4*. Nature 1996 Jul. 25; 382(6589):370-3), whereby it is predominantly cytoplasmic. However, an increase in intracellular calcium levels leads to its nuclear accumulation. Soderholm et al. (2011), showed by fluorescence microscopy that inhibiting nuclear import via Kpnβ1 prevented the nuclear accumulation of NFAT-GFP in response to stimulation with the calcium ionophore, ionomycin.

An assay for nuclear NFAT following ionomycin and Compound A treatment was carried out, using an NFAT-luciferase reporter that is activated by nuclear NFAT. The phorbol ester TPA was used to co-stimulate NFAT, as it has been shown previously that TPA and ionomycin elicit synergistic stimulation of NFAT luciferase activity (Northrop J P, Ullman K S, Crabtree G R. *Characterization of the nuclear and cytoplasmic components of the lymphoid-specific nuclear factor of activated T cells (NF-AT) complex*. J Biol Chem 1993 Feb. 5; 268(4):2917-23). While the AP1 and p65 luciferase assays represented in FIG. 15 revealed endogenous AP1 and p65 activities in response to Compound A treatment, NFAT was ectopically expressed in HeLa cells.

Figure 16:
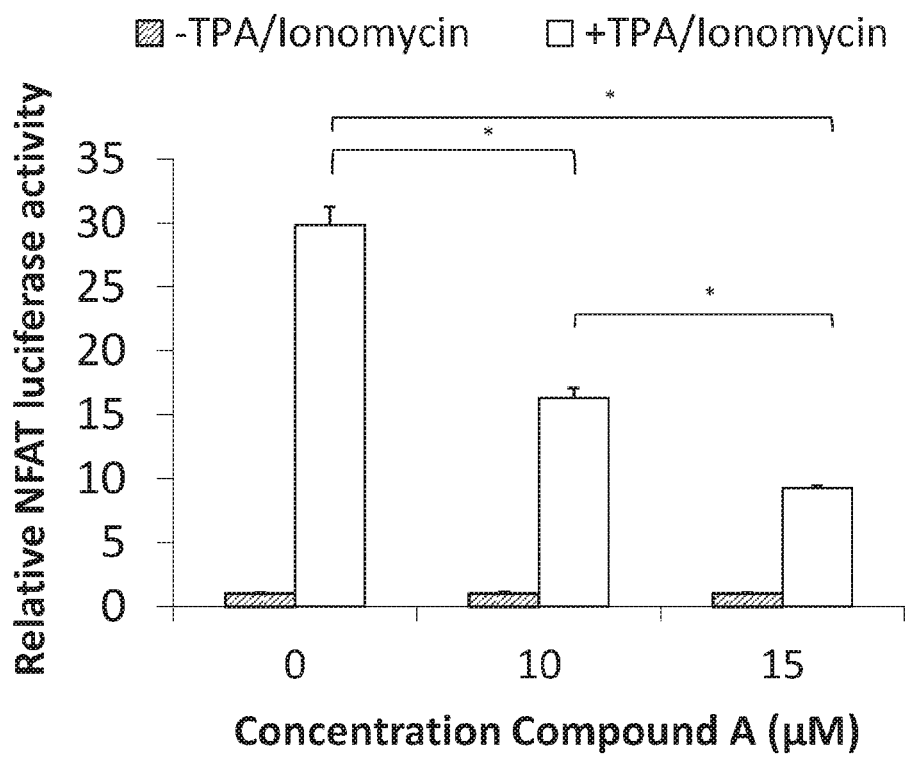
FIG. 16 is a bar graph of the NFAT transcriptional activity of NFAT-transfected HeLa cells transfected with an NFAT reporter plasmid, incubated in the presence of TPA and Ionomycin (+TPA/Ionomycin) or without TPA and Ionomycin (−TPA/Ionomycin) and in the presence of different concentrations of Compound A (*$p<0.05$)
Figure 17:
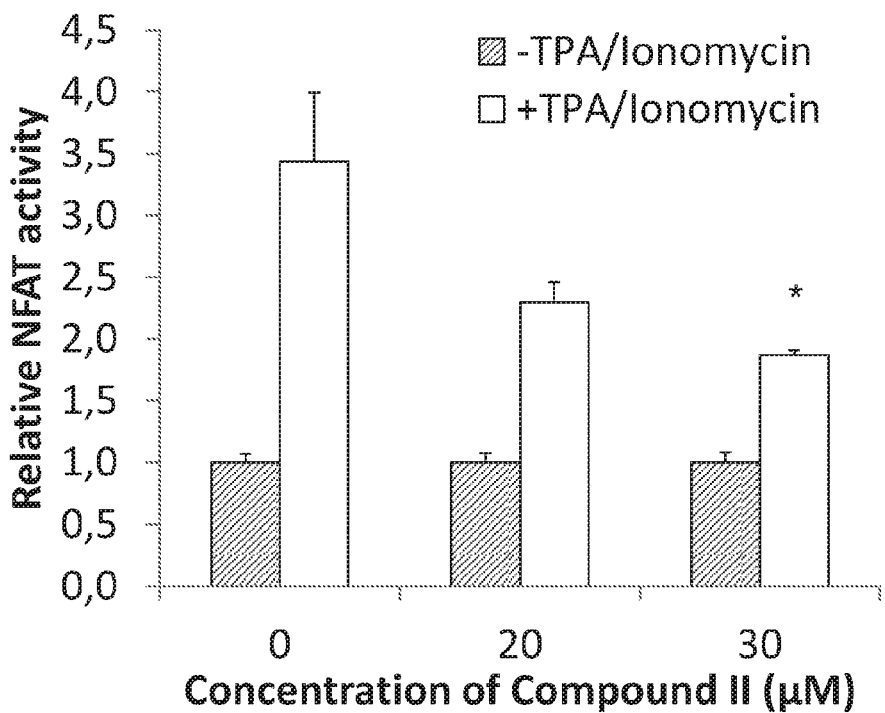
FIG. 17 is a bar graph of the NFAT transcriptional activity of NFAT-transfected HeLa cells transfected with an NFAT reporter plasmid, incubated in the presence of TPA and Ionomycin (+TPA/Ionomycin) or without TPA and Ionomycin (−TPA/Ionomycin) and in the presence of different concentrations of Compound II (*$p<0.05$)
Figure 18:
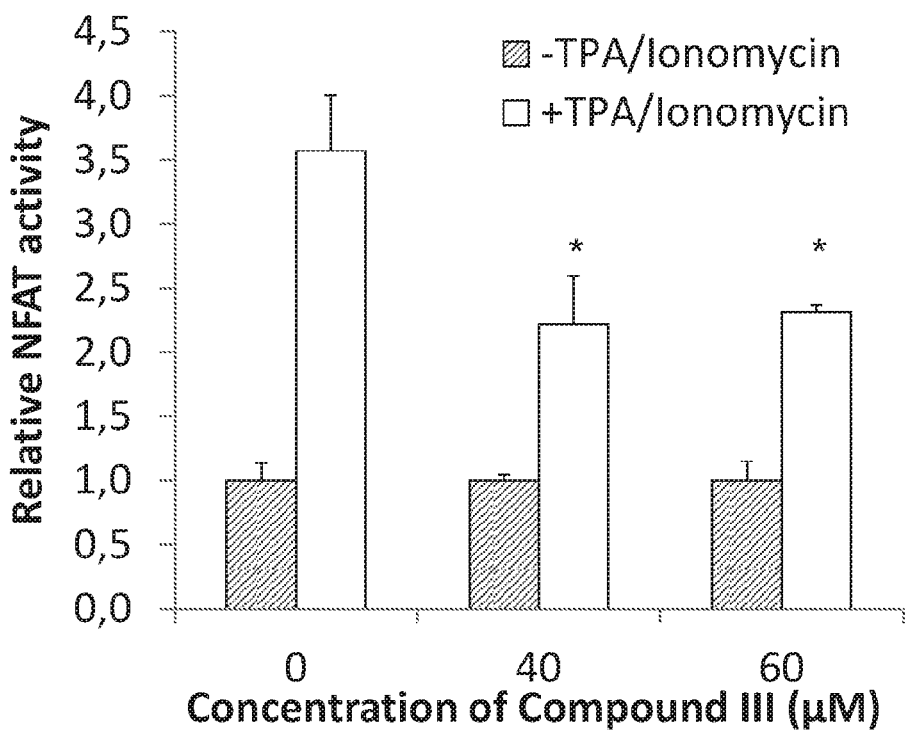
FIG. 18 is a bar graph of the NFAT transcriptional activity of NFAT-transfected HeLa cells transfected with an NFAT reporter plasmid, incubated in the presence of TPA and Ionomycin (+TPA/Ionomycin) or without TPA and Ionomycin (−TPA/Ionomycin) and in the presence of different concentrations of Compound III (*$p<0.05$)
Figure 19:
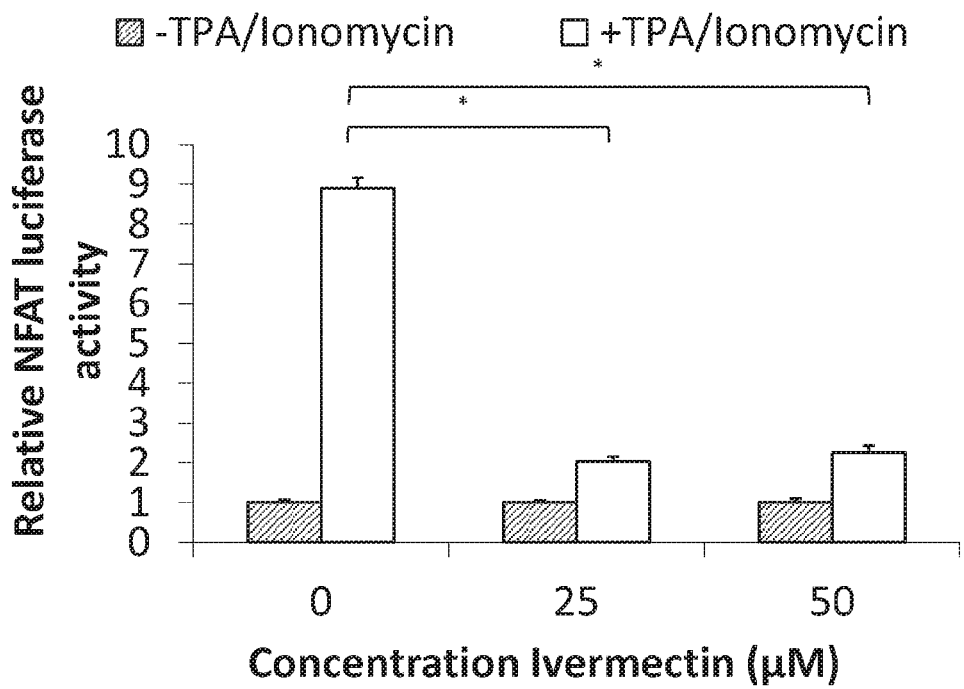
FIG. 19 is a bar graph of the NFAT transcriptional activity of NFAT-transfected HeLa cells transfected with an NFAT reporter plasmid, incubated in the presence of TPA and Ionomycin (+TPA/Ionomycin) or without TPA and Ionomycin (−TPA/Ionomycin) and in the presence of different concentrations of Ivermectin, which is a known inhibitor of Kpnβ1/Kpnα2-mediated nuclear transport and serves as a positive control.
Figure 20:
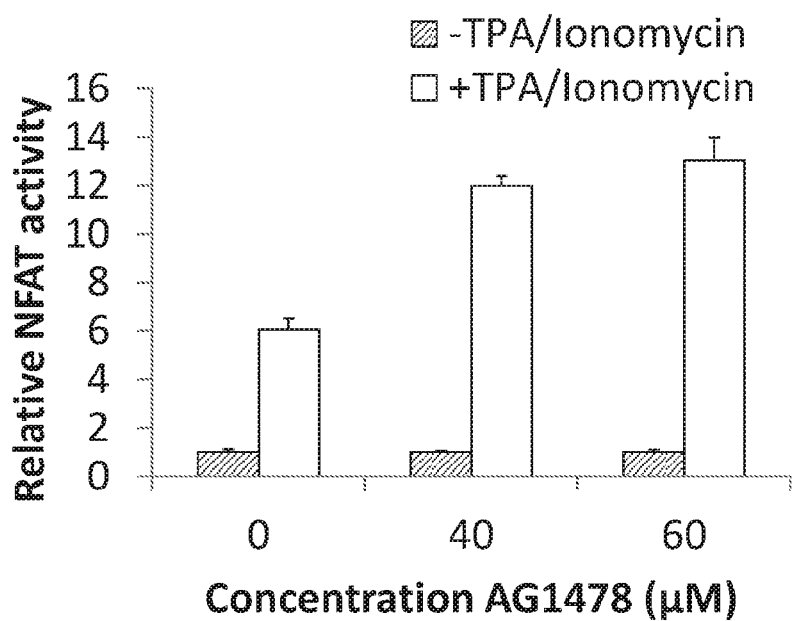
FIG. 20 is a bar graph of the NFAT transcriptional activity of NFAT-transfected HeLa cells transfected with an NFAT reporter plasmid, incubated in the presence of TPA and Ionomycin (+TPA/Ionomycin) or without TPA and Ionomycin (−TPA/Ionomycin) and in the presence of different concentrations of the Epidermal Growth Factor Receptor (EGF-R) inhibitor, AG1478, which serves as a negative control.

Results showed that stimulation of NFAT-transfected HeLa cells with TPA and ionomycin resulted in a significant increase in activation of the NFAT reporter, due to the nuclear import of NFAT (FIG. 16). Treatment with Compound A, Compound II and Compound III significantly diminished NFAT activation, in a dose-dependent manner, presumably due to its inhibition of NFAT nuclear import (FIGS. 16, 17 and 18). As a positive control, cells were treated with Ivermectin, a broad-spectrum anti-parasitic that was recently found to inhibit Karyopherin α/β-mediated nuclear transport (Wagstraff et al., 2012; Wagstaff K M, Rawlinson S M, Hearps A C, Jans D A. *An AlphaScreen®-based assay for high-throughput screening for specific inhibitors of nuclear import*. J Biomol Screen 2011 February; 16(2):192-200). An NFAT assay was performed using Ivermectin, and similar to the result obtained with Compound A, the induction of NFAT activity was significantly diminished upon Ivermectin treatment (FIG. 19). Finally, NFAT activation was measured after treatment of cells with AG1478, a EGF-R inhibitor, and no change in NFAT activation was observed (FIG. 20).

Cancer Cell Death Via Cell Cycle Arrest and the Induction of Apoptosis

To identify a nuclear import inhibitor with anti-cancer activity, the cell-killing effect of Compound A was tested using a panel of cell lines of various origins. Amongst the cell lines tested, Compound A did not show preference for a particular cancer type and was found to kill cancer cell lines of cervical (HeLa, CaSki), oesophageal (WHCO1, WHCO5, WHCO6), ovarian (A2780, CP70 and OVCAR3) and breast origin (MDA-MB-231, MCF7) with an IC50 of approximately 10 µM (Table 11).

TABLE 11

IC50 values for cancer cells, transformed cells and non-cancer cells treated with Compound A.

| Cell type | Cell line | IC50 (µM) | 95% Confidence Interval |
|---|---|---|---|
| Cancer/ transformed | CaSki | 9.33 | 6.51-13.38 |
| | HeLa | 8.77 | 8.12-9.38 |
| | KYSE30 | 8.84 | 8.45-9.26 |
| | KYSE150 | 11.72 | 10.48-13.10 |
| | WHCO1 | 10.62 | 9.55-11.81 |
| | WHCO5 | 9.09 | 8.11-16.15 |
| | WHCO6 | 11.99 | 11.42-12.57 |
| | A2780 | 5.79 | 5.63-5.95 |
| | CP70 | 7.70 | 7.58-7.81 |
| | OVCAR3 | 10.46 | 10.21-10.71 |
| | MCF12A | 12.74 | 9.19-17.65 |
| | MCF7 | 9.33 | 8.34-10.42 |
| | MDA-MB-231 | 7.92 | 7.32-8.56 |
| | SVWI38 | 10.44 | 9.95-10.95 |
| Non-cancer | FG0 | 21.42 | 18.86-24.32 |
| | WI38 | 24.02 | 18.96-30.43 |
| | DMB | 31.38 | 29.32-33.59 |

Importantly, Compound A showed elevated toxicity in the cancer or transformed cell lines relative to the non-cancer fibroblast lines. It showed about 2- to 3-fold selectivity toward cancer or transformed cell lines over non-cancer fibroblast cells.

Figure 21:
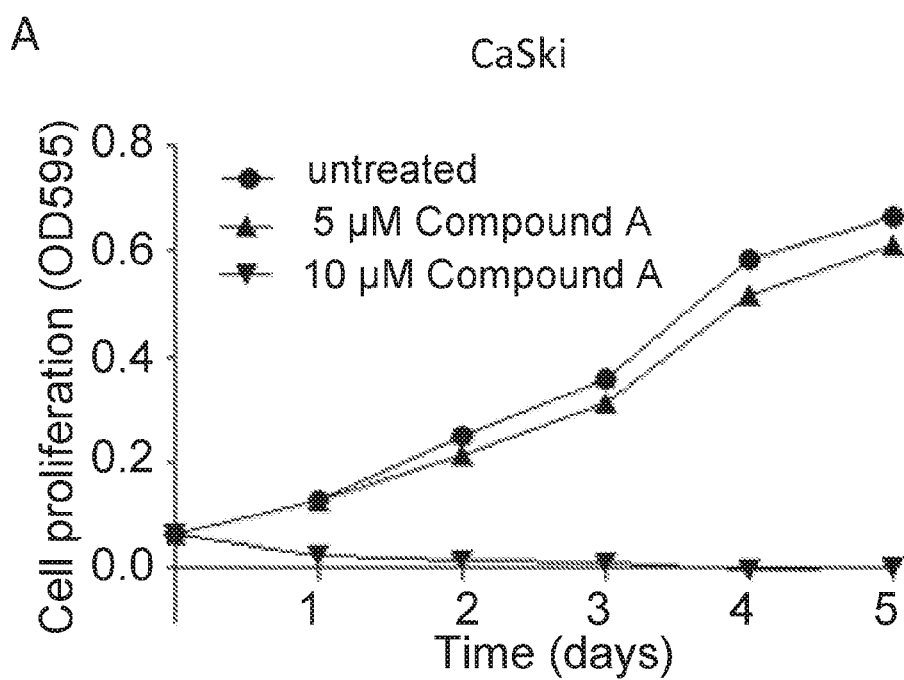
FIG. 21 is a collection of plots of cell proliferation monitored using the MTT assay of CaSki (A), HeLa (B), KYSE30 (C) and WHCO6 (D) cancer cells as well as DMB (E) and FG0 (F) non-cancer cells when treated with increasing concentrations of Compound A.
Figure 21:
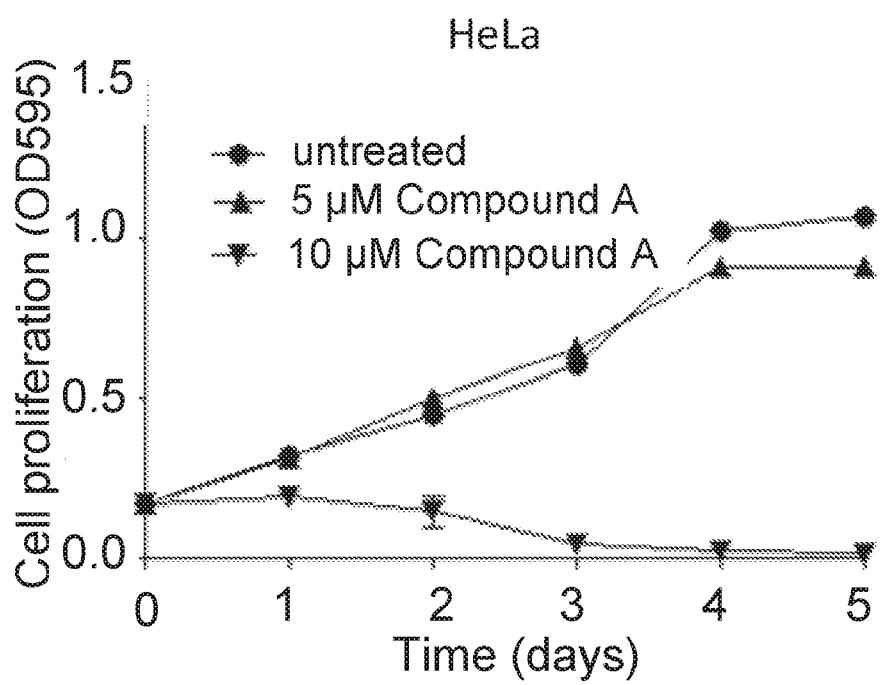
Figure 21:
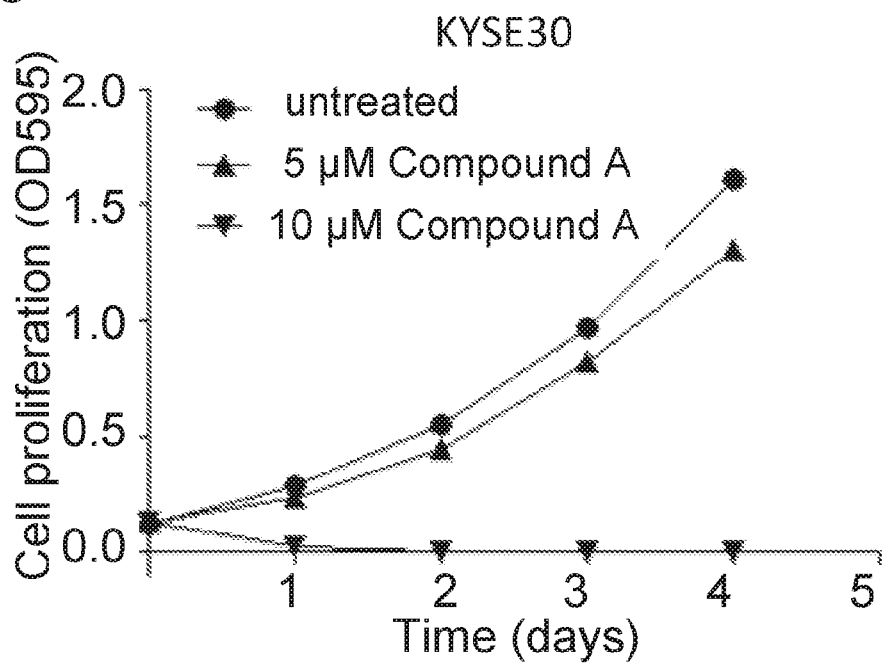
Figure 21:
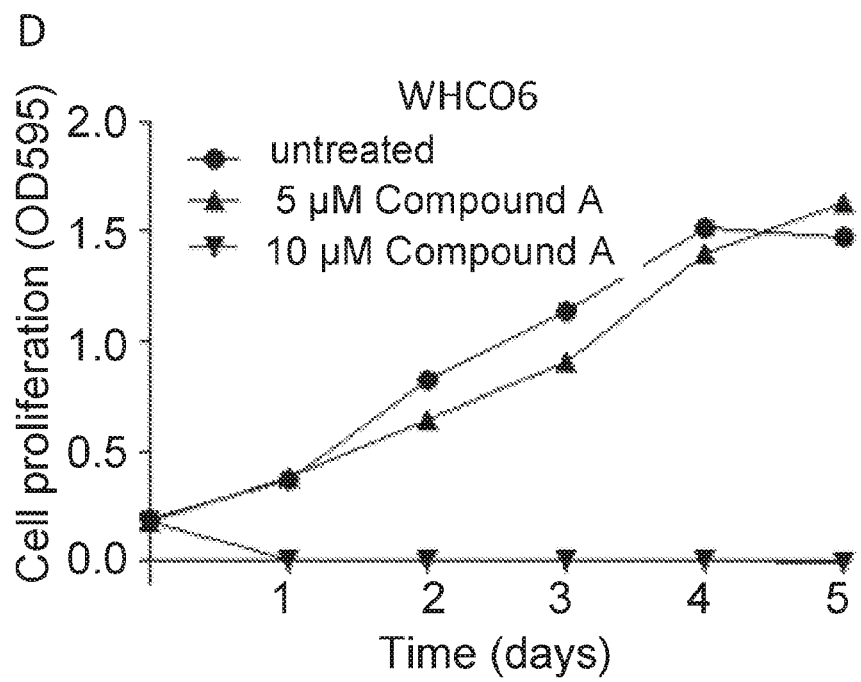
Figure 21:
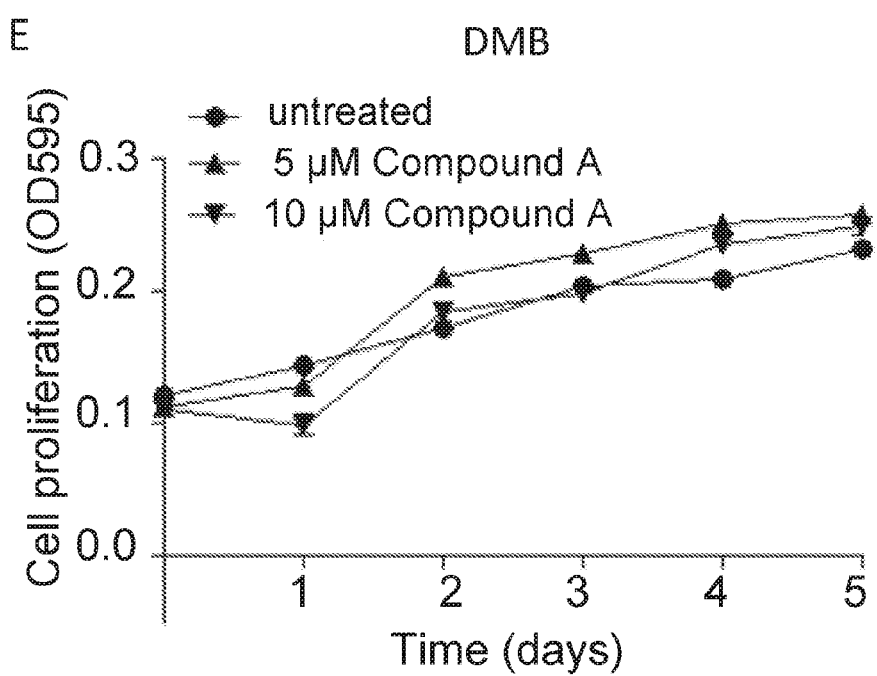
Figure 21:
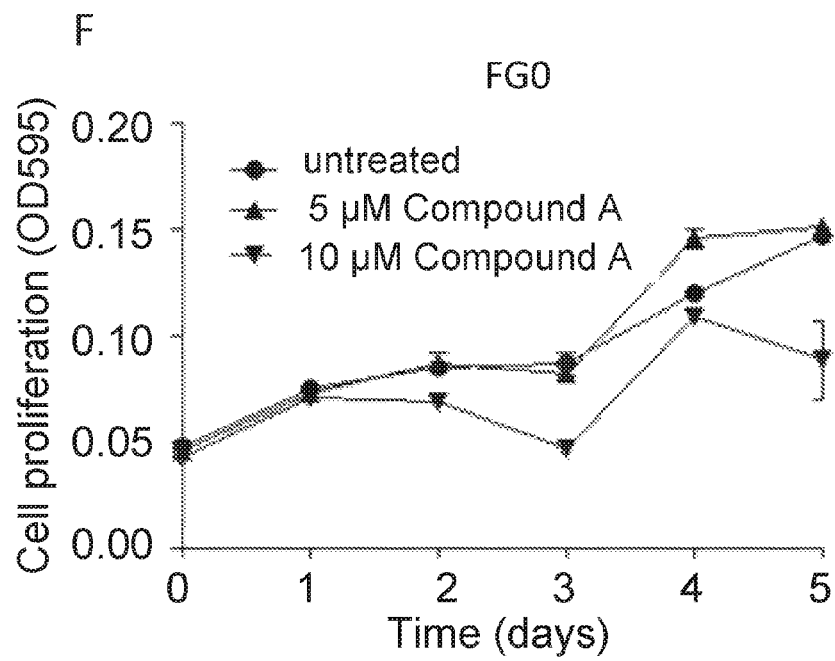

To confirm that Compound A was more effective at killing cancer cells compared to non-cancer cells, representative cancer (cervical and oesophageal) and non-cancer cell lines, were grown in the presence of Compound A, and cell proliferation measured daily for five days, using MTT assays. FIG. 21 shows that the cancer cells were highly sensitive to Compound A, as within 24 hour complete cell death was observed at concentrations of 10 and 15 µM Compound A (FIG. 21 A-D). This effect was sustained for the full 5 day time period, confirming that there was no population of cells that recovered from the treatment.

Figure 22:
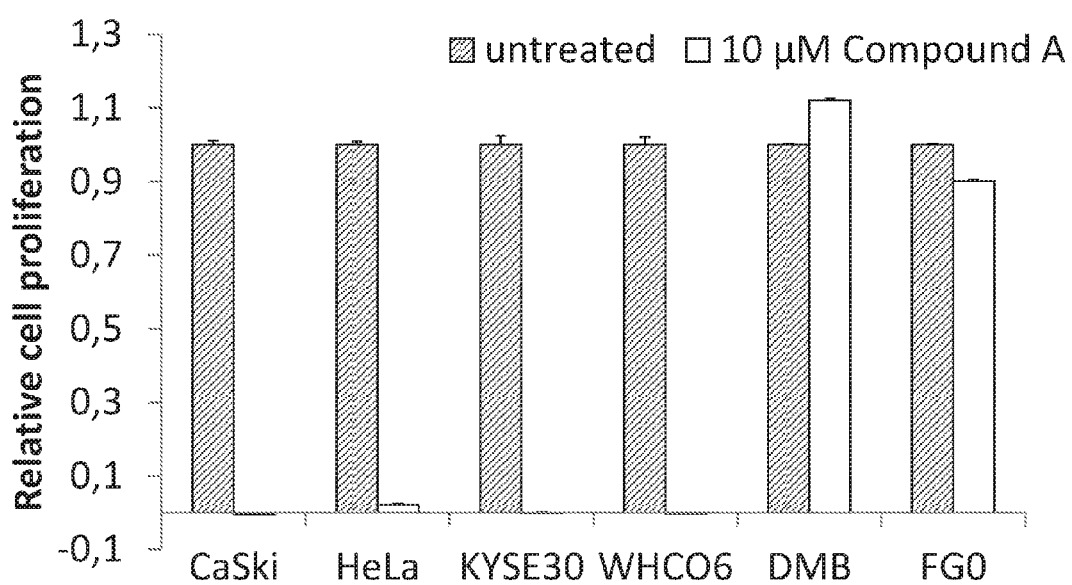
FIG. 22 is a bar graph of the cell proliferation of cancer cells (Caski, HeLa, KYSE30 and WHCO6) and non-cancer cells (FG0 and DMB) in the presence of 10 μM Compound A or absence of Compound A.

Non-cancer fibroblast cells, however, proliferated relatively normally in the presence of 10 µM Compound A, but at 15 µM Compound A cell death occurred within 24-48 hours (FIGS. 21 E and F). The result points to the differential sensitivity of cancer and non-cancer cells to Compound A, where at 10 µM Compound A treatment the cancer cells underwent 100% cell death, whilst the non-cancer cells were relatively unaffected (FIG. 22). While the IC50 for the non-cancer cells was previously shown to be in the 20-30 µM range, the cells died at 15 µM due to fewer cells being plated in the cell proliferation assay.

Figure 23:
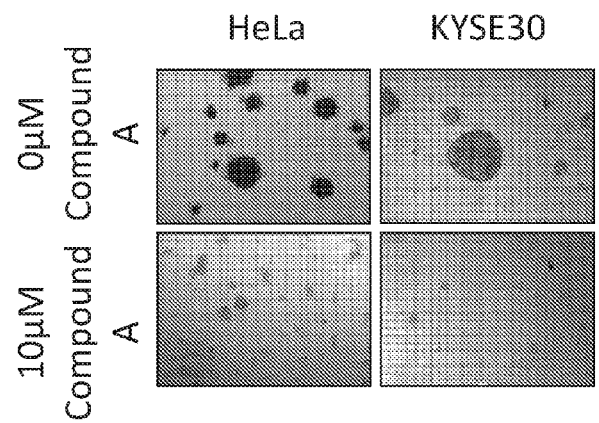
FIG. 23 is photographs of anchorage-independent colony formation of HeLa and KYSE30 cells grown in the presence or absence of 10 μM Compound A.

The anchorage-independent proliferation of cancer cells was measured in response to Compound A treatment, as cells grown in this manner are more representative of tumour cells in vivo. Cells were grown on polyheme-coated plates and cell proliferation monitored 9 days after treatment, using MTT assays. It was observed that both cervical and oesophageal cancer cells were unable to form colonies when grown in the presence of 10 µM Compound A, unlike their untreated counterparts (FIG. 23), confirming the ability of Compound A to block both anchorage-dependent and anchorage-independent proliferation of cancer cells.

Figure 24:
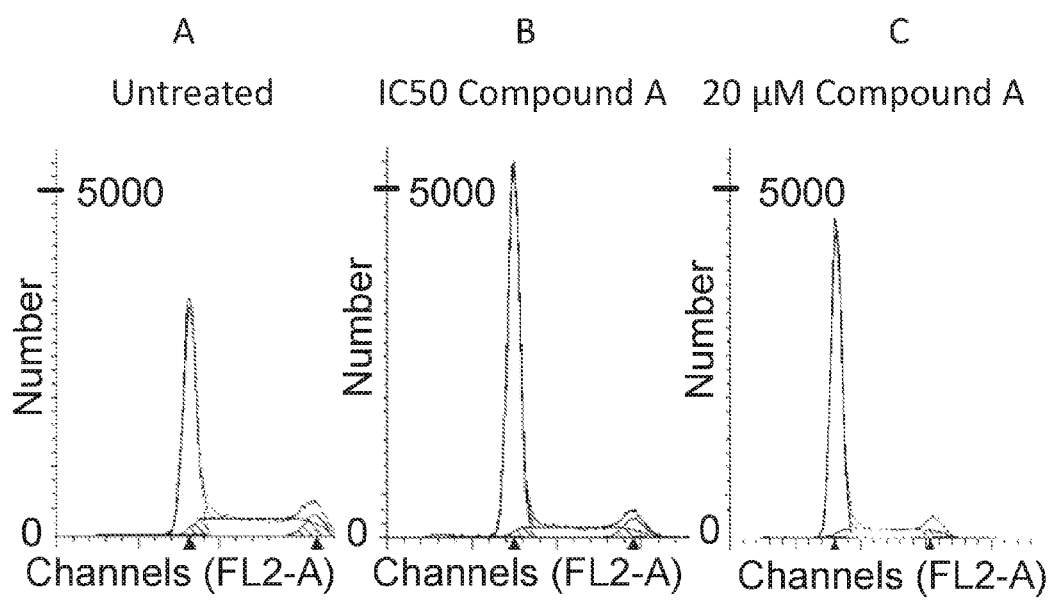
FIG. 24 is a cell cycle analysis of untreated CaSki cells (A) or CaSki cells treated with 10 μM Compound A (B) or 20 μM Compound A (C)
Figure 25:
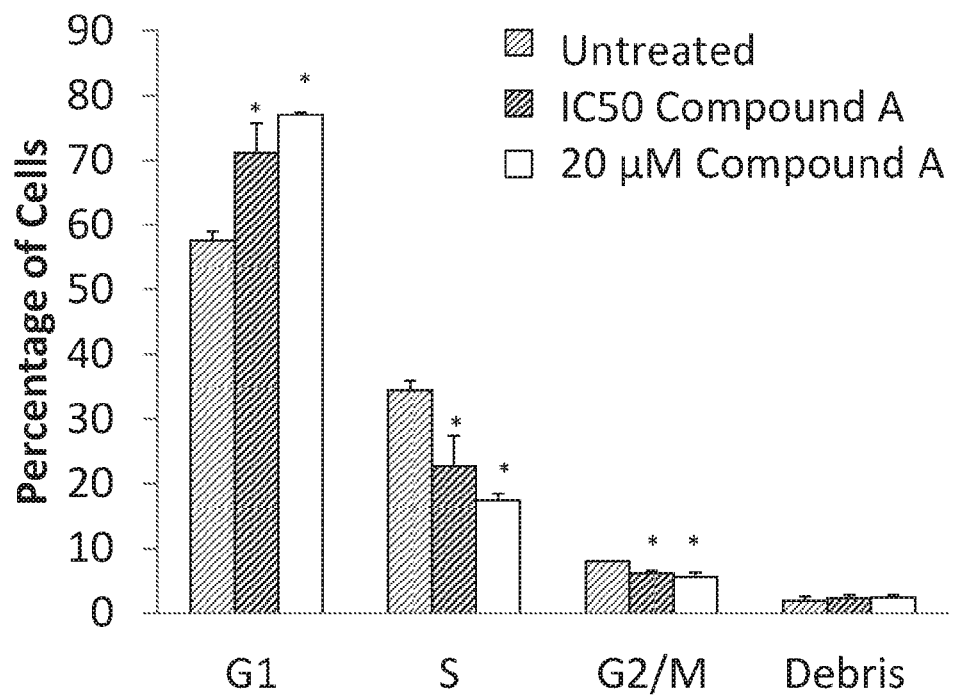
FIG. 25 is a bar graph of the percentage of cells in the various phases of the cell cycle based on cell cycle analyses performed in the presence of DMSO, the IC50 concentration of Compound A and 20 μM Compound A (*p<0.05)
Figure 26:
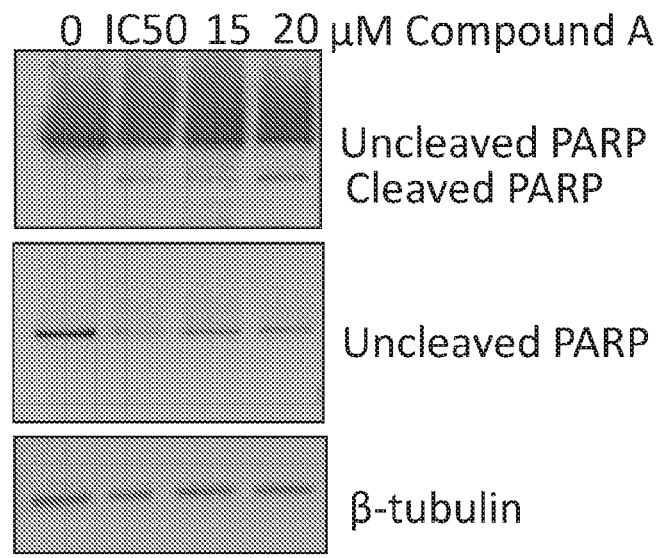
FIG. 26 is a Western Blot analysis showing that Compound A treatment results in PARP cleavage as an indicator of apoptosis, wherein β-tubulin was used as a protein loading control.

The mechanism of Compound A-induced cell death was investigated. A cell cycle analysis was performed and it was found that Compound A treatment resulted in an increase in the percentage of cells in the G1 stage of the cell cycle, and a corresponding decrease in the percentage of cells in the S and G2/M stages (FIGS. 24 and 25). The induction of a cell cycle block suggested that apoptosis might be activated; hence the cleavage of poly(ADP-ribose) polymerase (PARP-1) was measured by Western Blot analysis as an indicator of apoptosis. PARP-1 is cleaved into fragments of 89 and 24 kDa during apoptosis (Duriez P J, Shah G M. Cleavage of poly(ADP-ribose) polymerase: a sensitive parameter to study cell death. Biochem Cell Biol 1997; 75(4):337-49). Compound A treatment resulted in an increase in the levels of the 89 kDa cleaved PARP, associated with a decrease in the presence of uncleaved Parp (of 113 kDa) (FIG. 26). The 24 kDa band was not visible.

Figure 27:
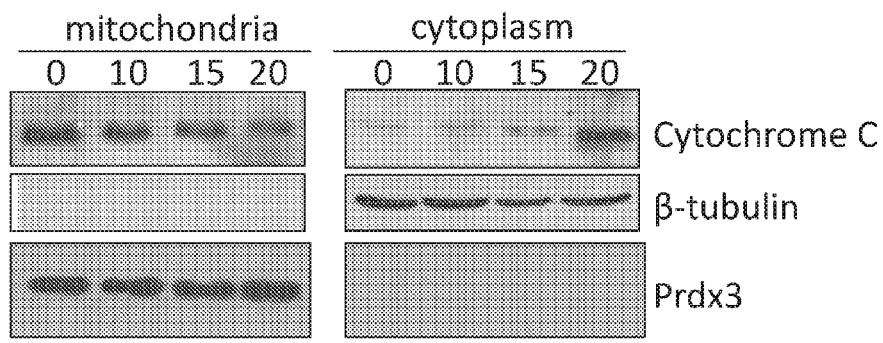
FIG. 27 is a Western Blot analysis showing an increase in Cytochrome C release into the cytoplasm with a concomitant decrease in mitochondrial Cytochrome C levels, suggesting activation of the intrinsic apoptotic pathway, wherein β-tubulin and Peroxiredoxin 3 (Prdx3) were used as loading controls for cytoplasmic and mitochondrial proteins, respectively, and to confirm the purity of the fractions.

To independently confirm the induction of apoptosis, Cytochrome C subcellular localisation was investigated, as its release into the cytoplasm is a characteristic feature of apoptosis mediated by the intrinsic mitochondrial pathway. Cells were treated with Compound A and mitochondrial and cytoplasmic protein fractions harvested for Western Blot analysis. Interestingly, Compound A treatment resulted in the release of Cytochrome C from the mitochondria into the cytoplasm, in a dose-dependent manner (FIG. 27), suggesting that the intrinsic mitochondrial pathway is activated upon Compound A treatment and responsible for cancer cell death.

Inhibition of Tumour Growth in Cancer Xenografts Models

Figure 28:
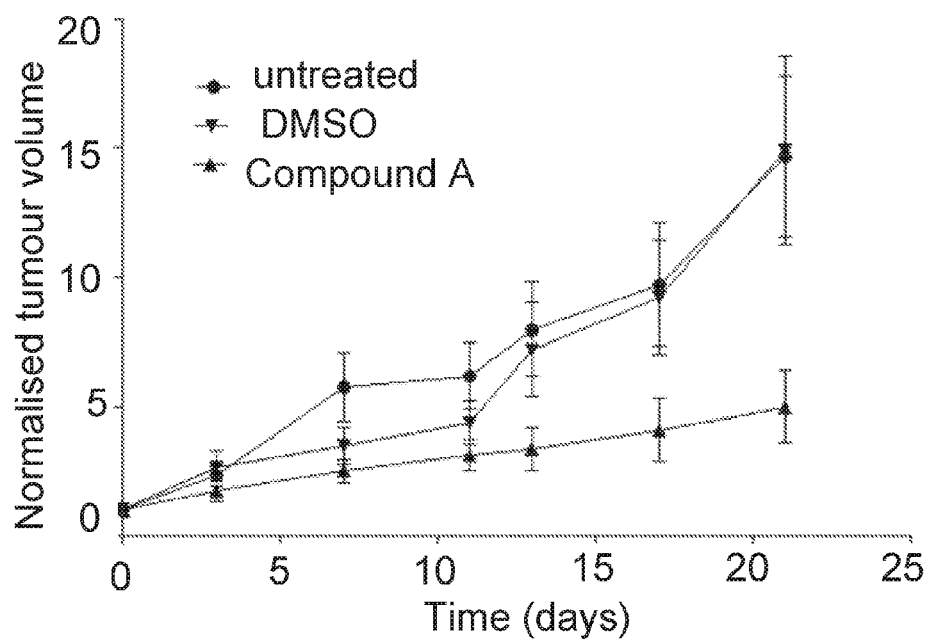
FIG. 28 is a plot of normalised tumour volume in WHCO6 tumour-bearing mice that were either left untreated, treated with vehicle (DMSO) or Compound A every 2-3 days for 3 weeks; and, FIG. 29 is a plot of the body mass of the tumour-bearing mice measured every day during the course of the treatment described with reference to FIG. 28.
Figure 29:
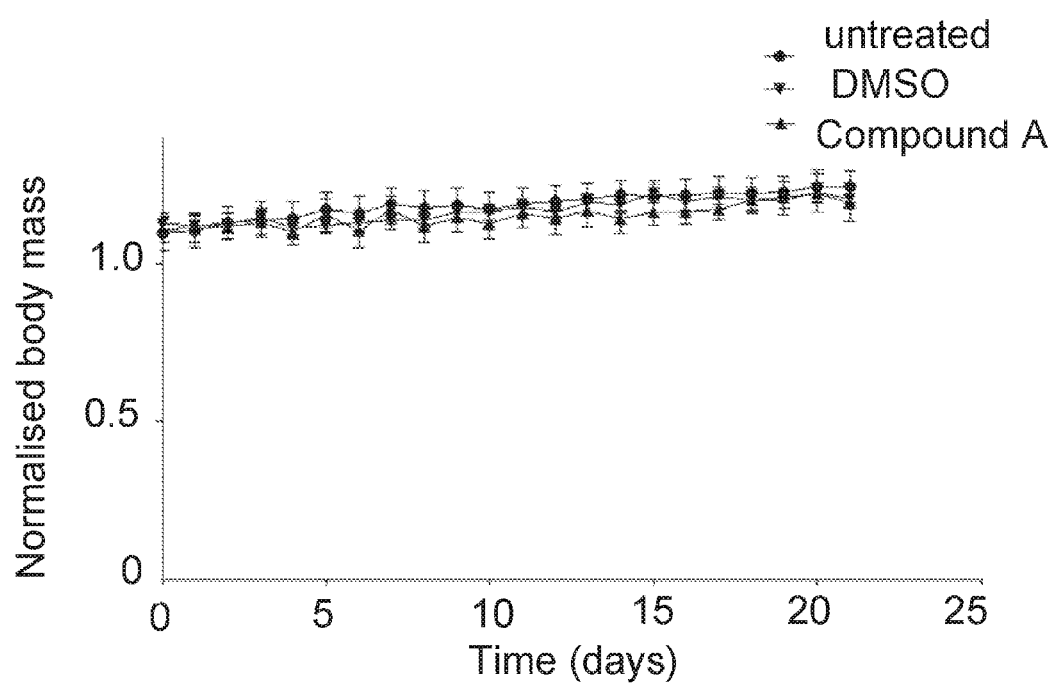

Compound A displays cytotoxicity in vitro and it was further found that it has antitumor activity in vivo as demonstrated with mouse xenograft models. Mice were inoculated with WHCO6 cancer cells and, once tumours had reached a palpable size, the mice were treated with vehicle (dimethyl sulfoxide (DMSO)) or Compound A every three days and tumour size monitored for three weeks. Compound A treatment significantly inhibits tumour growth (FIG. 28). The body mass of the mice did not change over the course of the treatment with Compound A and the mice appeared healthy, suggesting that no adverse side-effects were experienced (FIG. 29).

To confirm the ability of Compound A to block nuclear import, cells were treated with Compound A and the localisation of Kpnα2, an accessory protein that forms a heterodimer with Kpnβ1 in the nuclear import pathway, was monitored. Kpnα2 is thus largely reliant on Kpnβ1 for its nuclear import. Moreover, the rapid shuttling of Kpnα2 into the nucleus makes it a particularly useful tool for the identification of nuclear import inhibitors. Both exogenous and endogenous Kpnα2 were examined after Compound A treatment and it was found that its nuclear localisation was reduced in the presence of Compound A, implicating Compound A as an inhibitor of Kpnβ1-nuclear transport. In analysing GFP-Kpnα2 after Compound A treatment, however, it was found that there was variation in the extent of GFP-Kpnα2 mislocalisation to the cytoplasm, for example, some cells displayed solely cytoplasmic GFP-Kpnα2 after Compound A treatment, while others displayed nuclear and cytoplasmic GFP-Kpnα2. It is reported that the nature of the Kpnα2-Kpnβ1 interaction changes at different phases of the cell cycle (Yasuhara N, Takeda E, Inoue H, Kotera Yoneda Y. *Importin alpha/beta-mediated nuclear protein import is regulated in a cell cycle-dependent manner. Exp Cell Res* 2004 Jul. 1; 297(1):285-93). Therefore, the use of asynchronous cells in the experiment, could have resulted in different Kpnα2 localisation in different cells.

Furthermore, it has been demonstrated that Kpnα2 can enter the nucleus in a Kpnβ1-independent manner, possibly to perform its other non-nuclear transport functions, such as its regulation of mitotic progression (Miyamoto Y, Hieda M, Harreman M T, Fukumoto M, Saiwaki T, Hodel A E, et al. *Importin alpha can migrate into the nucleus in an importin beta-and Ran-independent manner. EMBO J* 2002 Nov. 1; 21(21):5833-42). It is thus possible that in the absence of Kpnβ1 function some Kpnα2 is still able to enter the nucleus.

The localisation of other Kpnβ1-dependent cargo proteins was also analysed after Compound A treatment, including the transcription factors, NFY, AP-1, p65 and NFAT, all of which displayed diminished nuclear import upon Compound A treatment. These transcription factors have all been shown to rely on Kpnβ1 for nuclear import in previous studies, and the inhibition of their nuclear import after Kpnβ1 inhibition highlights the extent to which nuclear import inhibition can affect cellular processes crucial for cancer cell survival.

Since Compound A was found to inhibit nuclear import, its cell-killing effect was analysed and it was found that cancer cells were more sensitive to Compound A treatment than non-cancer cells. There is substantial evidence in the literature that nuclear export inhibitors targeting Crm1 exhibit potent anti-cancer activity but only minimal effects on normal cells (Etchin J, Sun Q, Kentsis A, Farmer A, Zhang Z C, Sanda T, et al. *Antileukemic activity of nuclear export inhibitors that spare normal hematopoietic cells. Leukemia* 2013 January; 27(1):66-74; Mutka S C, Yang W Q, Dong S D, Ward S L, Craig D A, Timmermans P B, et al. *Identification of nuclear export inhibitors with potent anti-cancer activity in vivo. Cancer Res* 2009 Jan. 15; 69(2):510-7; Pathria G, Wagner C, Wagner S N. *Inhibition of CRM1-mediated nucleocytoplasmic transport: triggering human melanoma cell apoptosis by perturbing multiple cellular pathways. J Invest Dermatol* 2012 December; 132(12): 2780-90).

Moreover, the inhibition of Kpnβ1 using siRNA also results in the selective killing of cancer cells, whereby apoptosis is induced after Kpnβ1 silencing in cancer cells, while the inhibition of Kpnβ1 in non-cancer cells has only a minor effect on cell biology (Van der Watt et al., 2009). As the goal of cancer therapy is to promote the death of cancer cells without causing too much damage to normal cells this selectivity is advantageous for the development of anti-nuclear import drugs with therapeutic potential. The selectivity may derive from the increased nuclear transport rates in cancer cells compared to normal cells, and thus increased reliance on the nuclear transport machinery (Kuusisto et al., 2012). Alternatively, it is also possible that the selectivity towards cancer cells is due to the cancer cells being "primed" to undergo apoptosis (closer in proximity to the apoptotic threshold) compared to normal cells (Ni Chonghaile T, Sarosiek K A, Vo T T, Ryan J A, Tammareddi A, Moore V G, et al. *Pretreatment mitochondrial priming correlates with clinical response to cytotoxic chemotherapy. Science* 2011 Nov. 25; 334(6059):1129-33).

The inhibition of nuclear import is associated with an increase in multiple markers of apoptosis in cancer cells. These include a G1 cell cycle arrest, the cleavage of Parp and the release of Cytochrome C from the mitochondria into the cytoplasm. Cytochrome C release is a feature of the intrinsic mitochondria-mediated apoptosis pathway, suggesting that Compound A treatment results in the activation of the intrinsic apoptotic pathway. The intrinsic apoptosis pathway is similarly induced after Crm1 inhibition in leukemic cells (Etchin et al., 2013) and Kpnβ1 inhibition in cervical cancer cells using siRNA (Angus et al., 2014). Apoptosis is likely induced by the mislocalisation of key proteins after nuclear import inhibition and thus the disruption of cellular homeostasis. Compounds A to K are, thus, novel inhibitors of nuclear import and they display anti-cancer activity in vitro. Compound A displays anti-cancer activity in vitro and in vivo.

The novel inhibitors of nuclear import have anti-cancer effects. Particularly, compounds of formula I to XVI described above have been found to display anti-cancer effects. It has been demonstrated that Compound A displays anti-cancer activity by inhibiting nuclear import and inducing cell apoptosis. It will be appreciated by someone skilled in the art that Compounds B to K induce cell apoptosis by the same or a similar mechanism of action as that of Compound A. It has been shown that Compound II and Compound III have anti-cancer activity associated with nuclear import inhibition. It has also been demonstrated that compounds V to XVI, listed in Table 5 above, have anti-cancer activity.

There is consequently provided for the use of compounds of general formula I (including compounds A to K) and Compounds II to XIV, their stereoisomer or salts in treating cancer. More specifically, there is provided for the use of compounds A to K and Compounds II to XIV in treating cancer, in particular, but not limited to, cervical, oesophageal, ovarian, and breast cancer.

More specifically, it is foreseen that Compounds of general formula I, wherein $R_1$ is a C2-C5 alkyl group, branched or unbranched, optionally functionalised with a substituent selected from the group consisting of an amine, an imidazole, an alcohol or a morpholine; and wherein $R_2$ is a hydrogen or a methyl group and Compounds II-XVI, their stereoisomers or salts may be used for treating abnormal growth or neoplasm.

The compounds of general formula I, wherein $R_1$ is a C2-C5 alkyl group, branched or unbranched, optionally functionalised with a substituent selected from the group consisting of an amine, an imidazole, an alcohol or a morpholine; and wherein $R_2$ is a hydrogen or a methyl group and Compounds II-XVI, their stereoisomers or salts may be used for treating a malignant neoplasm or cancer selected from the group consisting of gastric cancer, lung cancer, liver cancer, melanoma, Hodgkin's disease, non-Hodgkin's lymphomas, acute or chronic lymphocytic leukaemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukaemia, primary brain carcinoma, malignant melanoma, small-cell lung carcinoma, stomach carcinoma, colon carcinoma, malignant pancreatic insulinoma, malignant carcinoid carcinoma, malignant melanoma, chorio carcinoma, mycosis fungoide, head or neck carcinoma, osteogenic sarcoma, pancreatic carcinoma, acute granulocytic leukaemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, prostatic carcinoma, larynx cancer, vulvar cancer or testicular cancer.

Such use in the treatment of cancer entails compounds A to K inhibiting activity of a nuclear transport protein, Kpnβ1, by binding to Kpnβ1 in cells in an overlapping binding site on Kpnβ1 which binds karyopherin α (Kpnα) and GTP-binding nuclear protein Ran. In treating cancer, compounds A to K, Compound II and Compound III inhibit the import of proteins and transcription factors Kpnα, AP-1, P65, NFAT into the nucleus of a cell and induces cell apoptosis, selectively in cancer cells.

A therapeutically effective concentration of any one of compounds A to K and Compounds II to XIV, their stereoisomers or salts, or a combination of any two or more of Compounds A to K and Compounds II to XIV, their stereoisomers or salts ranges depending on the compound but is less than 100 µM, preferably less than 50 µM, most preferably about 10 µM.

Compounds of formula I to XIV, their stereoisomers or pharmaceutically acceptable salts can be administered to a patient in need thereof in any suitable manner and may form the active ingredient of a medicament. Such medicament may include other ingredients including adjuvants and carriers.

Any one of the compounds of formula I to XIV, their stereoisomers or salts or a combination of any two or more of the compounds of formula I to XIV their stereoisomers or salts, can be used as a medicament to treat cancer and can also be used in the manufacture of a medicament for use in the treatment of cancer. Such medicaments can have any suitable form.

There is thus also provided a method of treating cancer which includes administering to a patient in need thereof a therapeutically effective amount of any one of the compounds of formula I to XIV, their stereoisomers or salts, or a combination of any two or more of the compounds of formula I to XIV, their stereoisomers or salts.

It is considered that cervical, oesophageal, ovarian and breast cancer, in particular, may be treated using one or more of the compounds of formula I to XIV, their stereoisomers and/or pharmaceutically acceptable salts, but it is envisaged that other forms of cancer, as listed above, may also be treated with these compounds.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A method for inhibiting karyopherin beta 1 activity in a patient, which comprises administering to a patient in need thereof a therapeutically effective amount of a compound of Formula I:

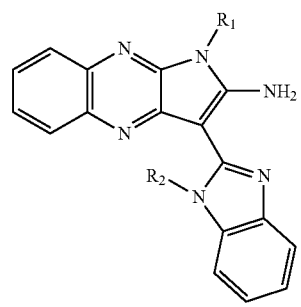

Formula I or a pharmaceutically acceptable salt thereof,
wherein:
$R_1$ is a branched or unbranched C2-C4 alkyl group, optionally functionalized with a substituent selected from the group consisting of an amine, an imidazole, an alcohol and a morpholine; and
$R_2$ is a hydrogen or a methyl group.

2. The method as claimed in claim 1, wherein the patient suffers from cancer.

3. The method as claimed in claim 2, wherein the cancer is selected from the group consisting of cervical cancer, esophageal cancer, ovarian cancer and breast cancer.

4. The method as claimed in claim 1, wherein $R_1$ is selected from:

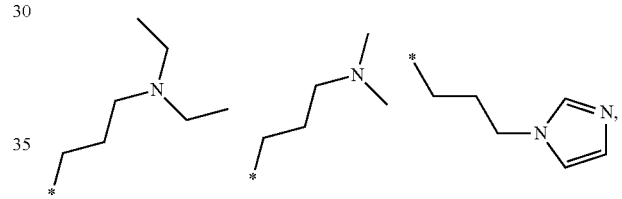

an ethyl group, a propyl group, a butyl group, an iso-butyl group, a propanol group and

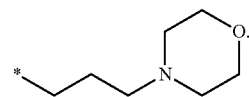

5. The method as claimed in claim 1, wherein the compound of Formula I is selected from:

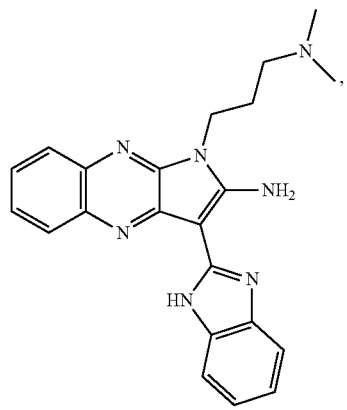

45
-continued
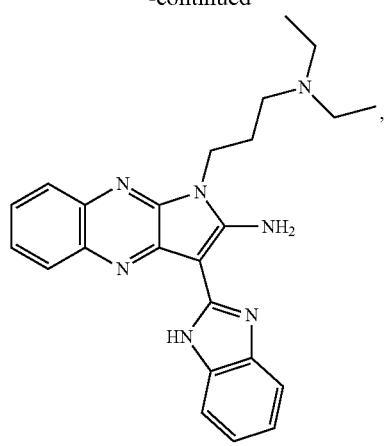
46
-continued
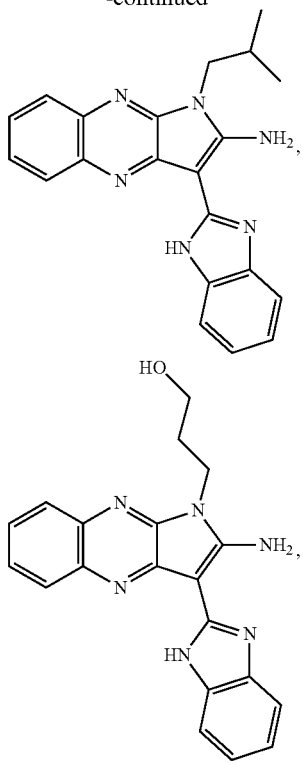
and

-continued
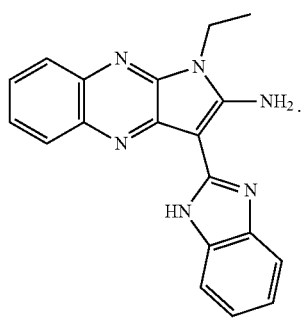
* * * * *